United States Patent [19]

Hannah et al.

[11] 4,365,303

[45] Dec. 21, 1982

[54] METHOD AND APPARATUS FOR DETERMINING THE NATURE OF AN UNKNOWN CHEMICAL SUBSTANCE

[75] Inventors: Robert W. Hannah, Newtown; John P. Coates, Easton; Abraham Savitzky, Wilton, all of Conn.; Michael A. Ford, Maidenhead; Harry V. Carter, Beaconsfield, both of England

[73] Assignee: The Perkin-Elmer Corporation, Norwalk, Conn.

[21] Appl. No.: 119,237

[22] Filed: Feb. 7, 1980

[51] Int. Cl.$^3$ .................. G06F 15/20; G01N 21/22
[52] U.S. Cl. ................................. 364/498; 364/300
[58] Field of Search ............ 364/497, 498, 499, 200, 364/900, 300

[56] References Cited

U.S. PATENT DOCUMENTS 4,093,991 6/1978 Christie, Jr. et al. .......... 364/498 X
4,267,572 5/1981 Witte ................................. 364/498

OTHER PUBLICATIONS

Data Acquisition and Processing for High-Resolution Mass Spectrometry Using a Small Nondedicated Computer; Christie, Smith & McKown; Chemical Instrumentation, 5(1), pp. 43-58 (1973-1974).

Primary Examiner—Edward J. Wise
Attorney, Agent, or Firm—S. A. Giarratana; F. L. Masselle; R. A. Hays

[57] ABSTRACT

Disclosed herein is method and apparatus for determining the nature of an unknown substance, which includes apparatus for entering a peak table of the spectrum of an unknown substance into computing apparatus, apparatus for adjusting the peak table to a first preselected standardized format, computing apparatus for comparing the so standardized peak table of the unknown with a first library of chemical structural units contained in memory in the computing apparatus, apparatus for making a list of the possible chemical structural units most closely corresponding to the unknown substance, apparatus for readjusting the peak table to a second preselected standardized format, apparatus for forming a file for the unknown substance including data corresponding to the readjusted peak table and to the list of possible chemical structural units, computing apparatus for comparing the file of the unknown substance with a second library containing files of known substances contained in memory in the computing apparatus, each known substance having a file containing data corresponding to its respective peak table in the second standardized format and to its respective chemical structural unit, and apparatus for outputting a list of known substances which most closely correspond to the unknown substance. In a form of the invention, apparatus is provided for adding data corresponding to a known substance to the second library contained in memory in the computing apparatus.

31 Claims, 5 Drawing Figures

METHOD AND APPARATUS FOR DETERMINING THE NATURE OF AN UNKNOWN CHEMICAL SUBSTANCE

BACKGROUND OF THE INVENTION

This invention relates to analytical instruments, and more particularly to method and apparatus for determining the nature and characteristics of an unknown substance.

Heretofore, spectroscopists manually studied the spectrum of an unknown substance and, because of their personal knowledge and experience in the field, were able to identify certain characteristics thereof. They would then manually compare the test results with tables of spectra of known substances to determine which substance the unknown one most closely resembled. This was a tedious process and required substantial skill on the part of the spectroscopist.

Thereafter, attempts were made to use mechanical sorters and punched cards for spectral searching. Using the Sadtler spectra, which was the basis of part of the data set contained on the punched cards, one could not even consistently isolate known compounds. There were many reasons for this failure, e.g., sampling conditions were different, instrument calibrations were different, and the operator may not have used the same bands for input data as used by the original encoder of the data.

Attempts have been made to utilize computers to ease the burden of the spectroscopist. Such a system is described in an article by Hugh B. Woodruff and Morton E. Munk appearing in Research/Development, August, 1977 entitled: "Computer-Assisted Infrared Spectral Interpretation". This article describes a system wherein the pattern of peak position, intensity and shape for each of 169 different chemical classes is stored in memory in digital form. The spectroscopist observes the spectrum of the unknown compound under consideration and inputs into the computer the position of the peak maximums and a code number indicating the character of the peak, i.e., broad, average, sharp, strong, medium or weak. The computer then compares this input with each of the 169 classes in storage to output one of five possible confidence levels for each class tested. The article then points out that information from other sources is generally necessary to complete the spectroscopic analysis.

SUMMARY OF THE INVENTION

In view of the foregoing, the present invention is intended to provide method and apparatus for determining the nature of an unknown substance, which is an improvement over the systems used heretofore, as will become apparent as the description proceeds.

According to the invention, in one form thereof, there is provided apparatus for determining the nature of an unknown substance, which includes means for entering a peak table of a spectrum of an unknown substance into computing apparatus, means for adjusting said peak table to a first preselected standardized format, means for comparing the so standardized peak table of the unknown with a first library of chemical structural units contained in memory in the computing apparatus, and means for making a list of the possible chemical structural units most closely corresponding to said unknown substance. In addition, this apparatus includes means for readjusting the peak table to a second preselected standardized format, means for forming a file for said unknown substance including data corresponding to the readjusted peak table and to said list of possible chemical structural units, means for comparing the file of the unknown substance with a second library containing files of known substances contained in memory in the computing apparatus. Each known substance has a file containing data corresponding to its respective peak table in said standardized format and to its respective chemical structural units. Further, the apparatus includes means for outputting a list of known substances which most closely correspond to said unknown substance.

In one form of the invention, the means for entering the peak table of the spectrum of an unknown substance includes means for entering said peak table from a spectrophotometer, and in another form of the invention the means for entering the peak table includes means for manually entering the table using a keyboard module. In still another form of the invention the means for entering the peak table includes the use of a digitizer module, while still another form of the invention utilizes means for entering the peak table from a microfloppy disk containing peak tables generated at some previous point in time.

According to one aspect of the invention, the means for adjusting the peak table to a first preselected standard format includes: means for correcting the peak table for a sloping baseline, means for correcting the peak table using calibration data entered by the operator, means for correcting the peak table by normalizing to preselected peaks, and means for deleting from the peak table all of the peaks having a transmittance greater than a preselected threshold. Preferably, said preselected threshold is of the order of about 95% transmittance.

According to another aspect of the invention, the means for readjusting the peak table to a second preselected standardized format include: means for deleting from the peak table all of the peaks having a transmittance greater than a second preselected threshold, which, preferably, is of the order of about 85% transmittance. A further aspect of the invention is to restrict the range of wavenumbers in the peak table to a preselected range, which, preferably, is from about 1624 to about 600 cm$^{-1}$ wavenumbers.

Further, in one preferred form of the invention, the means for forming files for the unknown substance includes in addition to data corresponding to said readjusted peak table and to the list of possible chemical structural units, data corresponding to the physical state of the unknown, and data corresponding to the presence or absence of preselected non-organic elements in said unknown substance.

In still another form of the invention, the apparatus also includes means for comparing the file of the unknown substance with the second library containing files of known substances disregarding the possible chemical structural unit data, and means for outputting a second list of known substances which most closely correspond to the unknown substance. Further, in another form of the invention, means are provided for comparing the file of the unknown substance with the second library containing files of known substances, and outputting a third list of known substances the peaks of which most closely correspond to subsets of peaks of the unknown substance. Still further, according to another form of the invention, means are provided for comparing the file of the unknown substance with the second library containing files of known substances disregarding preselected bands of the peak table data and disregarding the possible chemical structural unit data, and means for outputting a fourth list of known substances which most closely correspond to the unknown substance.

Moreover, according to another aspect of the invention, there is provided, in addition, means for indicating the degree of correspondence of the unknown substance to each of the known substances in the list of known substances outputted.

Also, according to the invention, there is provided means for adding data corresponding to known substances to the library contained in the computing apparatus memory.

There has thus been outlined rather broadly the more important features of the invention in order that the detailed description thereof that follows may be better understood, and in order that the present contribution to the art may be better appreciated. There are, of course, additional features of the invention that will be described more fully hereinafter. Those skilled in the art will appreciate that the conception on which this disclosure is based may readily be utilized as the basis of the designing of other apparatus for carrying out the various purposes of the invention. It is important, therefore, that this disclosure be regarded as including such equivalent apparatus and methods as do not depart from the spirit and scope of the invention.

Several embodiments of the invention have been chosen for purposes of illustration and description, and are shown in the accompanying drawings forming a part of the specification.

DESCRIPTION OF THE PREFERRED EMBODIMENT

Figure 1:
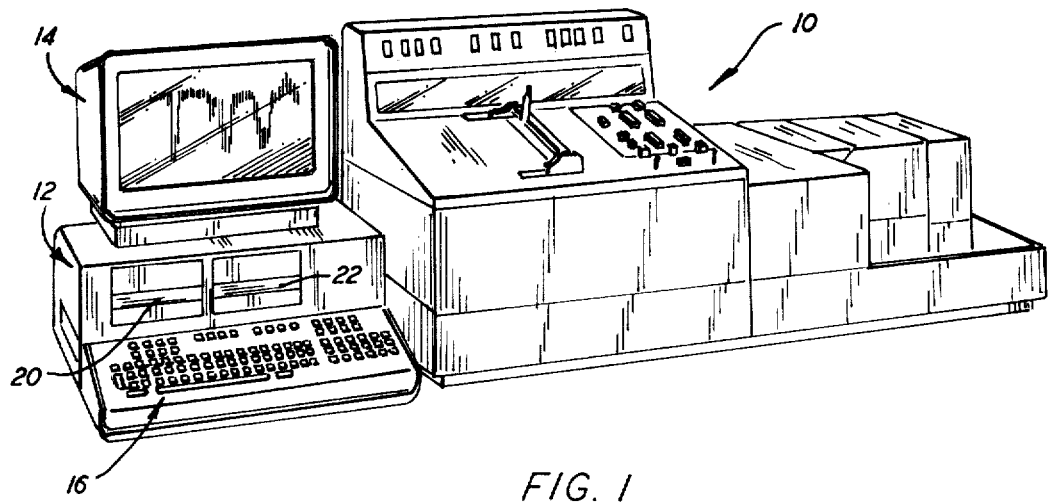
FIG. 1 is a prespective view of analytical apparatus incorporating the concepts of the present invention.

Although it will be recognized by those skilled in the art that the concepts of the present invention can be used in other types of analytical instruments, the description will be made in conjunction with an infrared spectrophotometer. When subjected to infrared radiation in the region of 4000 cm$^{-1}$ to 600 cm$^{-1}$, each functional group of an organic molecule gives rise to absorption bands throughout the spectrum. For a particular functional group, the absorption bands at certain wavelengths are specific, i.e., not the results of interferences, etc; and these bands provide the infrared "fingerprint" of the molecule.

The analytical instrument of the present invention may be considered as composed of a spectrophotometer 10, and a data station indicated generally at 11 comprising a data processing module 12, a visual display unit (VDU) 14, a keyboard module 16, a printer module 18 and a digitizer module 19. The spectrophotometer 10 may be of any suitable type such as, for example, models 281, 283, 580B, 28XB, X98 and X99B, as manufactured by The Perkin-Elmer Corporation. Communication between the operator and the data station 11 is accomplished via the keyboard 16. This keyboard, in addition to the standard terminal format, contains a number of special function keys, which allow the operator to select specific tasks from one of the application programs by depressing a single key on the keyboard, as will be discussed more fully hereinafter. The video screen 14 is used to display commands entered into the system by way of the keyboard 16, to show status and properties of data collected and to view spectra. The screen can be used to view a spectrum directly during a scan and to view the spectrum, which results after each step of data processing. The VDU, for example, may have a display capacity of 25 lines, with up to 80 characters per line. Line 25 is reserved exclusively for user commands and certain error messages.

Figure 2:
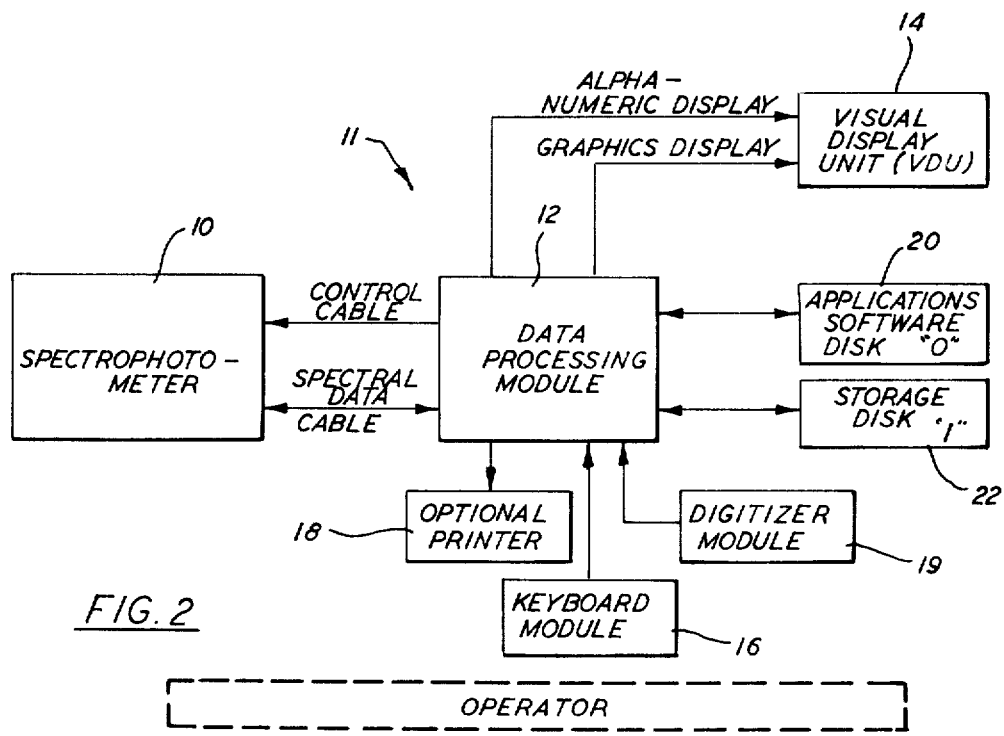
FIG. 2 is a block diagram of the apparatus of FIG. 1.

The data processing module 12 contains a Motorola 6800 based microprocessor with its associated electronics; a 64 K solid state memory (12 to 16K ROM, 48 to 52K RAM); a graphics printed circuit board; two microfloppy disk drives indicated at 20 and 22 FIG. 2; and a power supply.

The microprocessor is an 8-bit machine with a cycle time of two microseconds. The processor unit provides the functions necessary to operate the disk drives, handle data and communicate with the infrared spectrophotometer 10. In general, the operating programs as required by user commands are located on the "0" disk 20 on the left-hand side and bulk data files are stored or retrieved from the "1" disk 22 on the right-hand side of the data processing module 12. Each microfloppy disk typically has room for 80 K bytes of data and will store about 8 to 10 full-range spectra on each side. Several thousand peak tables, as will be discussed more fully hereinafter, are stored on each side of these disks. Spectral data files stored on a disk can be recalled in a matter of seconds into the system data memory (RAM) 36 associated with the data processing module 12, where they can be processed by the spectroscopy commands, displayed on the VDU screen and replotted if so desired on the instrument recorder 18. That is, the auxiliary printer can create a permanent record of alphanumeric data such as peak tables, data processing command sequences or any other alphanumeric VDU display of interest. A graphics printed circuit board (PCB), located within the data processing module 12, provides the graphic capabilities of the system and serves as the control interface between the spectrophotometer 10 and the data station 11. It contains a refresh-memory chipset for the VDU graphics display; the necessary video controls, compatible peripheral interfaces and instrument control drivers to transmit SCAN parameters, start/stop commands and PLOT initiation commands, as will be discussed hereinafter.

The digitizer module 19 provides a means for entering previously recorded spectra. A chart is placed on a magnetic sensor equipped metal plate and a cursor is used to enter coordinates of the chart grid. A magnifying eyepiece with cross-hairs is moved across the spectrum to locate and digitize each peak in turn. The user merely presses a button over each peak to instantly digitize the frequency and transmittance values.

Figure 3:
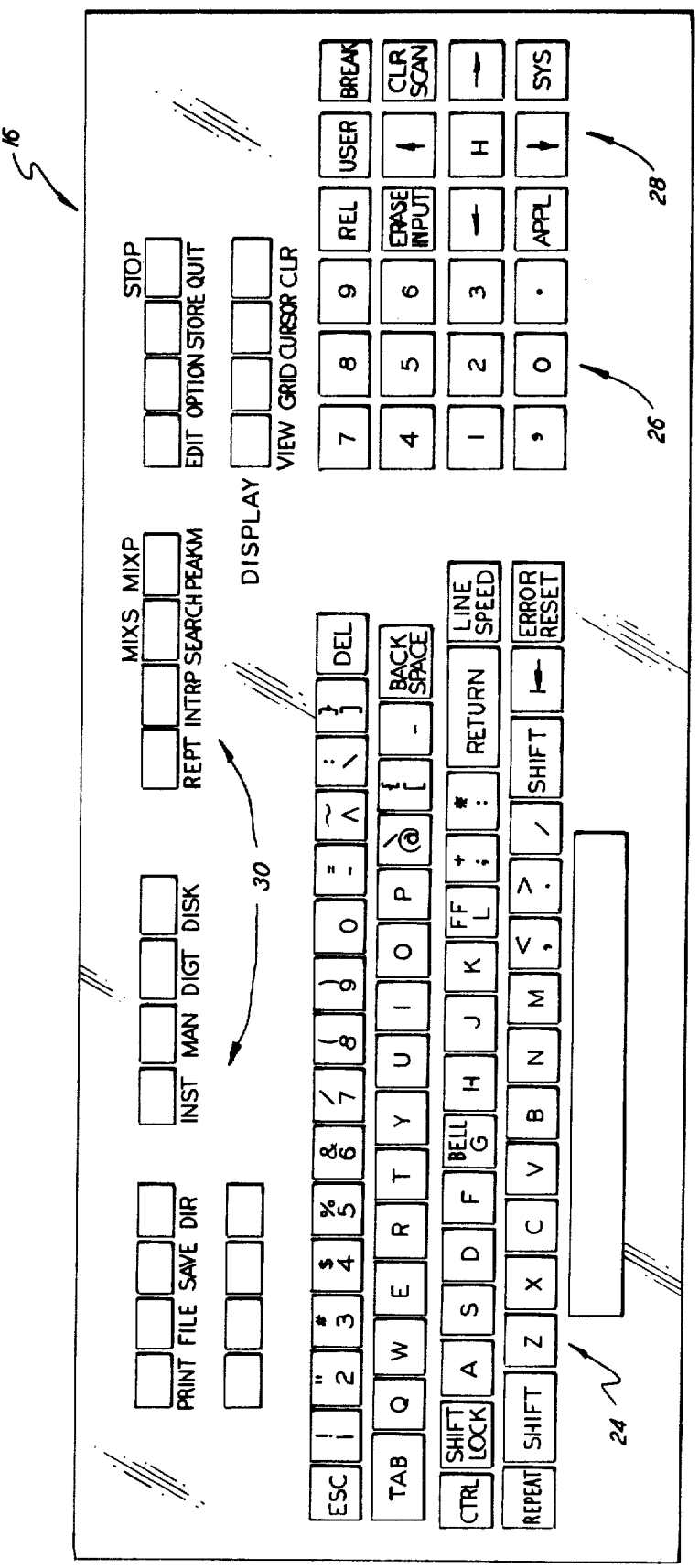
FIG. 3 is a view of the keyboard module of the apparatus of FIG. 1.

The keyboard module 16, which is connected to the processor module 12 via a flexible cable, is the means of entering user directives into the system. The layout of the keyboard is shown in FIG. 3. It is divided into four functional groupings. An alphanumeric entry group indicated at 24 contains sixty entry keys, which are arranged in the standard ASC11 format and includes the upper/lower case character set, punctuation marks, special symbols, numerals, shift, control, repeat, linefeed, return, backspace, escape and tab keys. A numeric entry pad indicated at 26 contains twelve keys, including the ten numerals, comma and decimal point. Twelve operational keyboard switches, indicated at 28, are used for display and cursor control, and for editing purposes. Special function switches indicated at 30 are utilized for the selection of specific spectroscopy data processing functions. In some cases these special command keys are used in conjunction with either the numeric or the alphanumeric keypads. As illustrated, the special function switches are applicable to the search applications program. If other programs are loaded, then these switches may initiate other special functions.

Figure 4:
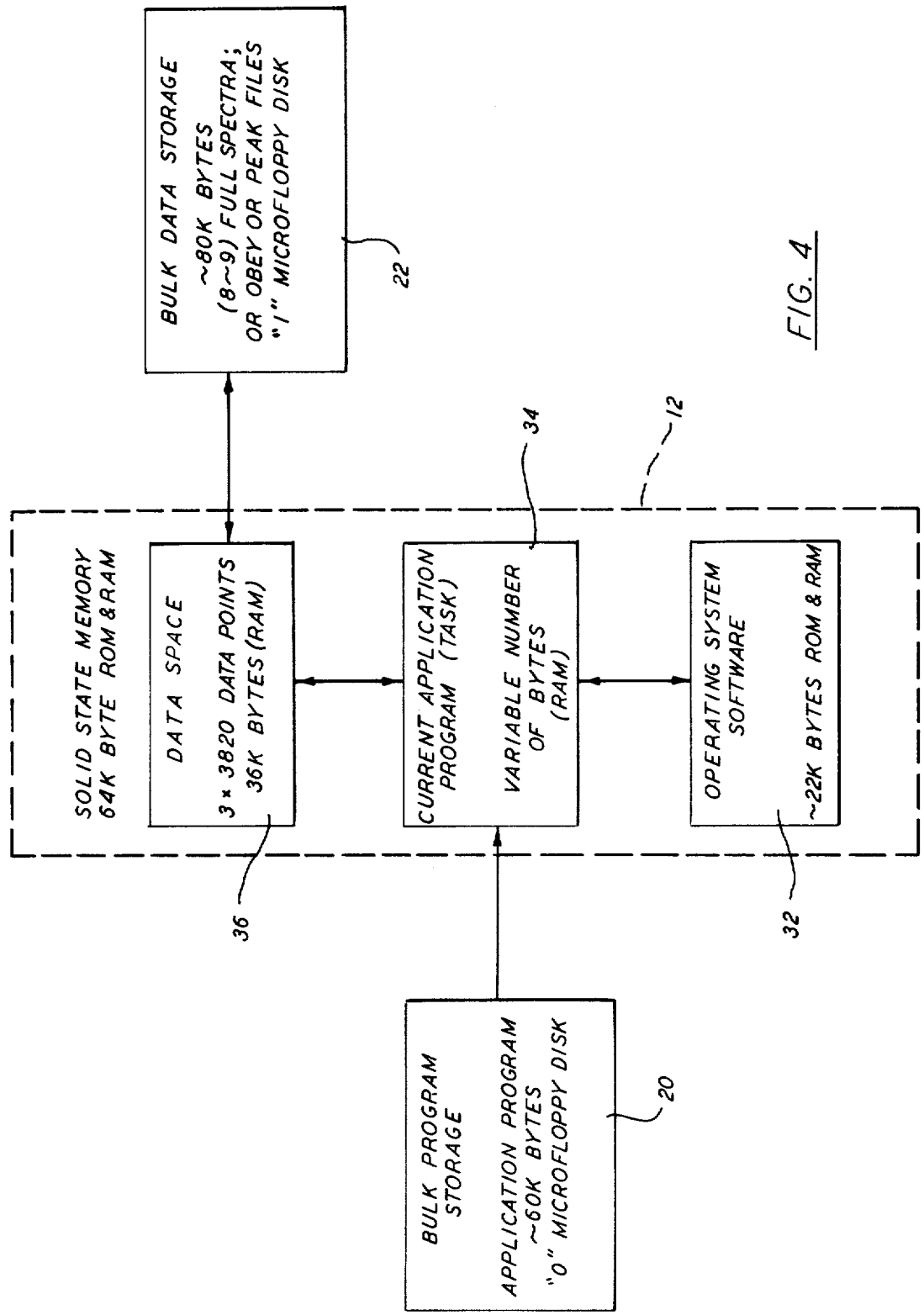
FIG. 4 is a block diagram illustrating the organization of the systems memory.

The data processing module 12 contains the systems memory, as shown in FIG. 4. The operating system portion of the software permanently resides in the ROM 32. The application program contains specific utility and application programs and sub-routines and is stored on one side of a microfloppy disk 20, which is loaded into a RAM 34 of the data processing module 12. This program is called the TASK and is developed to correspond to the particular type of spectrophotometer 10 being utilized. In the illustrative embodiment, this application program is approximately 70K bytes. At any given time one and only one user-selected command may be executed, i.e., the entry of a subsequent command has to wait for the completion of the preceding one. This same rule applies to the execution of the OBEY directive as well as to the other user commands; however, the pulling of the preselected routines of an OBEY command is performed sequentially and automatically. A set of utility programs contained on a separate microfloppy disk provides the user with the facility to perform diagnostic tests, copy disks, verify disks, and the like.

The data processing module 12 also contains a data storage space or RAM 36, FIG. 4, which communicates with the microfloppy disk 22. A total of 11,460 data points (ordinate values) can be stored in this RAM in three, equally divided zones X, Y, Z of 3,820 data points each. The size of the zones can be reset to any value within the total of 11,460.

The following table of commands are user initiated and relate to the various available data manipulation routines:

ABEX—Expands by a given factor and normalizes a spectrum in absorbance. A spectrum in percent transmission is converted to absorbance, multiplied by a given factor and reconverted to a percent transmission on a point by point basis.

ABST—Converts absorbance spectra to transmittance spectra.

ACCUM—Adds repetitively scanned spectra to accumulate ordinate changes for up to 250 scans.

ADD—Adds two spectra or a constant to a spectrum.

AVRAGE—Add repetitively scanned spectra and averages the results.

CHANGE—Allows modification of spectrum parameters and data.

CLEAR—Erases graphics (spectra) displayed on the VDU.

CNTENT—Reads the names of spectra stored on a disk and displays the results on the screen.

COPY—Transfers all or part of one data file to another data file.

CURSOR—Displays left or right or both wavenumber cursor with annotation. The cursor(s) is movable by the left/right arrow keys.

DIFF—Subtracts one spectrum from another after each has been converted to absorbance.

DIGT—Mode for entering data via the digitizer.

DIR—Search a data disk and display a table of contents.

DISK—Mode for retrieving peak tables from a data disk.

DIV—Divides a spectrum by a constant.

EDIT—Enter EDIT mode (for data correction.

FLAT—Treats spectral data to reduce effects of sloping baselines.

GRID—Displays wavenumber grid pattern over spectrum with a resolution dependent on spectral range selection. Each grid is annotated with the actual wavenumber display.

INST—Mode for entering data directly from a spectrophotometer.

INTRP—Initiates the possible structural unit (PSU) search only.

LIST—Displays a listing of available commands on the screen.

MAN—Mode for entering data via the keyboard.

MULT—Multiplies a spectrum by a constant.

OBEY—Initiates automatic execution of a series of commands of the spectroscopy software.

OPTION—Display option table with current values.

PEAK—Reduces bulk data to a table of spectrum peaks and respective ordinate values of the peak maxima.

PEAKM—Initiates spectral library band search only.

PLOT—Replots a spectrum from random access memory (RAM) onto the infrared instrument recorder with an operator specifiable set of ordinate and abscissa scaling factors.

PRINT—Allows production of hard copy of alphanumeric data from VDU screen on the printer accessory.

REPT—Return to peak table display.

RETRVE—Retrieves a spectrum by name from a microfloppy disk.

SAVE—Records (stores) a spectrum or a peak file on a microfloppy disk 22.

SCALE—Establishes plotting parameters.

SCAN—Scans a spectrum and retains the data in RAM 36.

SEARCH—Initiates library SEARCH routine.

SET—Allows adjustment of operating parameters.

STOP—Ends operation in spectroscopy software.

STORE—Writes information on spectral library disk 22.

SUB—Subtracts one spectrum or a constant from another spectrum.

SMOOTH—Reduces magnitude of rapid transients in spectral data and lessens effects of spectral noise.

STATUS—Indicates contents of RAM memory files 36 and shows the replot parameters.

TAAT—Converts spectra in absorbance to per cent transmission or the reverse.

TABS—Converts transmittance to absorbance.

TEST—Performs certain system tests.

TYPE—Prints a selected range of spectral data on the VDU screen 14.

VIEW—Displays one or more spectra in data files X, Y, or Z on the VDU screen.

MIXS and MIXP initiate a library search for mixtures and correspond to search and PeakM, respectively.

FILE puts the modified peak table from the editor to memory. QUIT exits the present operator.

Following the user directive, the operating parameters are entered as indicated on the VDU, followed by the actuation of RETURN key to execute the function called for. All parameter entries are alterable prior to execution.

The SCAN command is the primary command by which the operator may collect data from the infrared spectrophotometer 10 into the data processing module memory 36, FIG. 4. There are three data files designated X, Y and Z, and each contains sufficient space to store a spectrum scanned over the full range of from 4000 to 180 cm$^{-1}$ (3821 data points for each of the files X, Y and Z). Data collected in memory, as the spectrophotometer 10 scans, is displayed on the VDU screen 14, where the results can be monitored. After data has been collected into X, Y or Z, it will remain there until new data is collected in the same file, or power is removed from the data station 11. Loss of new data by overwriting or erasure of data files by power failure is easily avoided by recording the SCANned data on the microfloppy disk 22. Data storage is accomplished via the SAVE command. A five-space alphanumeric code name and up to a 50-space identification may be recorded with the data to aid in future retrieval. The RETRVE command is used to recall data from the microfloppy disk 22 into a particular file of the data processing module memory.

Spectral data collected under direction of ACCUM and AVRAGE commands are handled somewhat differently. Data is always collected into memory file X, and this file may be expanded as needed to overwrite data in files Y and Z. The number of scans which may be accumulated or averaged may range up to 250. The relative signal-to-noise ratio improves as a function of the square root of the number of scans collected. Consequently, ACCUM and AVRAGE are commands which are very useful in situations in which measurement of small changes in sample transmittance is of interest. The ACCUM command collects the changes in transmission during each scan and adds the new data to the accumulating data field. The average command performs in the same manner except that data is divided by the total number of scans accumulated for the final calculation of the spectrum. To collect data under direction of ACCUM or AVRAGE, one need specify the scan range, data interval (usually 1 cm$^{-1}$) and the number of scans to be accumulated or averaged. After data collection has begun, the system operates unattended for the duration of the process. Therefore, the otherwise tedious collection of data may be scheduled to occur at the operator's convenience, e.g., weekends and so on.

The next group of commands are ways of examining or observing data collected in the X, Y and Z files. The VIEW command employs the graphics capacity of the system to display the spectrum on the VDU screen 14 for operator inspection. The operator may optionally add to the display a cursor and/or a wavenumber grid. Either of two cursors can be moved on the viewed spectrum to positions of interest and the wavenumber positions of each cursor are displayed on the screen. This feature is especially useful when the operator desires to locate a particular peak maximum quickly or to determine a particular range of data for further manipulation. The contents of all three data files X, Y and Z can be viewed simultaneously in separate thirds of the screen by entering the command VIEW ALL. Alternatively, differences and similarities in two data files such as X and Y may be observed by entering the command VIEW X/Y. The differences in the corresponding ordinate values for each point of the X and Y files are then displayed on the VDU in white overlay on the dark background of the screen.

A hard copy of a spectrum contained in a data station memory file can be replotted on the instrument plotting system, FIG. 2, by actuating the PLOT command. A wide range of ordinate and abscissa expansion factors provides the operator with the facility to replot a spectrum with practically any scale desired.

The PEAK command produces a peak table on the screen in alphanumeric characters. The peak table is a listing of peak positions and ordinate values at peak maxima. The peak table may be recorded on a disk 22 and represents a way to save the essential spectral information in much less space on a microfloppy disk. A disk can hold several hundred peak tables. Consequently, the PEAK command is very important for search and retrieval activities in large spectral data libraries. Peak tables can be obtained in hard copy by actuating the PRINT command. The PRINT command will transfer the entire alphanumeric content of the VDU screen to paper. Therefore, the PRINT command will also provide hard copy output of directories of disk memories, contents of spectral files, or any other alphanumeric display from the screen.

The group of commands-FLAT, ABEX, DIFF, TAAT and SMOOTH- are ways to adjust or modify data in a spectral file. FLAT is designed to remove the effect of sloping baselines. Upward sloping baselines, for example, are commonly encountered in cloudy KBr pellet spectra. ABEX is a command designed to expand the ordinate size of a spectrum. When the data station carries out the ABEX command, digitized ordinate values of a spectrum registered in transmission are converted to absorbance, multiplied by a given factor and reconverted to transmission on a point-by-point basis. An expansion performed in this manner results in a spectrum of increased amplitude with no distortion of relative peak intensities. The ABEX command is particularly useful for expanding either dilute spectra or small differences between spectra.

The DIFF command is used to subtract one spectrum from another with optimum quantitative accuracy. During execution of the DIFF command, the data station 11 subtracts the absorbance values at corresponding wavenumbers between two spectral data files and leaves the resulting spectrum reported in absorbance. If the two spectra being subtracted are initially in transmission, the data station 11 converts digitized ordinate values of each spectrum on a point-by-point basis to absorbance, then completes the subtraction and files the result in absorbance.

Conversion of spectra from absorbance to transmittance and from transmittance to absorbance is accomplished by means of the TAAT command. Digital conversion of ordinate data, for example, from percent transmission to absorbance represents a method of obtaining an absorbance spectrum which is more accurate than analog conversion of percent transmission spectra. A frequent sequence of usage of the above commands would be DIFF, ABEX, TAAT, FLAT. This sequence would allow the user to obtain the difference between two spectra, expand the results to full scale in absorbance, convert the spectrum to transmittance and to remove effects of sloping baselines.

A spectrum processed to this extent may show some areas which would have a relatively poor signal-to-noise ratio. Noise can be reduced by the SMOOTH command which fits a moving point polynomial to the data and rounds rapid transients, e.g., noise. The SMOOTH command requires a degree of discretion from the operator to ensure that real data is not removed as well as noise.

Among the special capabilities of the infrared data station is the power to execute an extensive series of commands automatically. Such spectroscopy miniprograms are called OBEY files and allow the user to carry out a wide variety of operations on an infrared spectrophotometer attached to the data station 11 with completely unattended operation. Any of the spectroscopy software commands that an operator might wish to exercise can be written on the VDU screen with the EDIT software of the utility disk and recorded on a microfloppy disk designated for data collection. If the operator then pushes the OBEY special function key and types in the alphanumeric code he used to name his OBEY file, the data station 11 and infrared spectrophotometer 10 begin to carry out the instructions of the OBEY file. Comment lines can be inserted in OBEY files by beginning the command line with an asterisk. A single obey file might read as follows:

1.00=*THIS IS AN EXAMPLE OF AN OBEY FILE
2.00=SCAN X
3.00=VIEW X GRID
4.00=ABEX X
5.00=SMOOTH X, 3, Y
6.00=VIEW Y GRID

The analytical instrument of the present invention is provided with a search application program, which assists the spectroscopist in the actual interpretation of an infrared spectrum. Search is an applications function, which is designed to simplify the process of interpretation and identification of infrared spectra. From files of reference data, search is not only able to indicate the nature (functional groups) of an unknown organic substance, but also selects the names of compounds of similar type together with a rating that indicates the confidence level of the match. Compounds are excluded from selection if correlations are insufficient to satisfy the criteria demanded by the system.

The SEARCH applications function consists of three major sections: (1) data entry; (2) possible structural unit (PSU) search; and (3) spectral library search. In addition to these sections there are a number of other utility features contained in the search function to allow for such routines as the editing of data, creation of a library, saving data on a disk, etc. The commands to the SEARCH function are entered using the appropriate special function key 30, and auxiliary information is entered using the data station keyboard 24. Data may be entered into the SEARCH routine by the following four methods. These include entries directly from the spectrophotometer 10, a manual entry mode, the use of a spectral digitizer, and retrieving from a microfloppy disk 22 a peak table generated at some previous time.

In the first mode of data entry, from the spectrophotometer 10, the search software disk 20 is loaded and the INST function key is pushed on the keyboard module 16. The operator is instructed to scan from 4000 to 600 cm$^{-1}$ under normal survey conditions. As he scans, the spectrum is displayed on the screen in the VDU 14. It is noted that the bands should be reasonably intense and that they fall within about a 10 to 25% transmission value at the strongest peaks. Based on the quality of the spectral data, additional processing is carried out. One or more of the aforesaid data manipulation routines are employed to enhance the spectral data. The spectrum is first smoothed using the conventional 13 point cubic polynomial to cause some noise reduction. The background is flattened to account for any slopes in the higher wavenumber region, in particular, and then the ABEX routine is carried out. In this routine, the strongest band is expanded in absorbance until it has a transmission of 3% and the base line is set to 100 percent. After completion of these manipulations, the spectrum substantially fills the entire scale. The peak table is then created automatically under the instrument mode for this processed spectrum.

In the manual entry mode, a table of data composed of frequency and transmittance values for each of the peaks is entered in the edit environment. The operator simply presses the MAN key and edit is loaded from disk 22 into memory 35, FIG. 4. Reference information concerning baseline data for the particular spectrum is entered, and then a table of frequency and percent transmittance (%T) for each of the peaks in the spectrum is entered. The operator then terminates by typing END and proceeds with the next step.

In the digitizer mode of operation, the digitizer module 19 is used, wherein the spectrum under consideration is laid on a flat tablet and the cursor is moved from point to point corresponding to the peaks along the spectrum. Each of the XY cordinates of the individual peaks are converted into frequency and transmittance values and a peak table is created of the spectrum. In the digitizer mode, the operator must be instructed to enter not only baseline %T values at 3800 and 2000 cm$^{-1}$ (2.5 and 5u for linear wavelength), but also grid-related values for the points 3800 cm$^{-1}$, 0%T; 2000 cm$^{-1}$, 100%T; and 650 cm$^{-1}$, 0%T. (Corresponding wavelength values are 2.5u, 5u and 15u.) The maximum tolerance on the digitizer is 0.005" and the minimum 0.001". Tablet size should accomodate a full-size spectrum and should, therefore, be approximately 15×30" in the active area. By this means, spectra which are contained in libraries which already exist may be digitized and entered into the search library of the present instrument.

In the fourth mode of data entry, the user retrieves from a microfloppy disk peak tables generated at some previous time. Thus, it is possible to use an automatic sampler and have the instrument scan a series of samples contained therein and create peak tables for each of them, and to store these peak tables on a disk. The SEARCH software may then, at a later point in time, be loaded and each peak table recovered in turn from this disk and individually processed according to the SEARCH routine.

Regardless of the mode of data entry, it is necessary that for good interpretation of a spectrum, the sample must be very well prepared. Spectra entered into the routine must satisfy certain basic requirements. If poor data is entered into the routine, the results would be degraded. Thus, the criteria calls for absorbance band which do not bottom out, with the exception of the carbon hydrogen stretching region, but which have transmission of the order of magnitude of 1% for the strongest band in the system. The spectra may be either linear wavelength or 2:1 scale change if linear in wavenumber, if entered from the digitizer. Manual entry may be either in wavelength or wavenumber. In either the manual or digitizer mode, the operator must be directed from the display to indicate whether entry is in wavenumber or wavelength. Every peak between 4000 and 600 cm$^{-1}$ (or 2.5 to 15u) must be entered. The description of a peak includes the wavenumber positioned to the nearest wavenumber and a percent transmittance to the nearest percent. The lowest percent transmittance must be greater than 1% thus putting some restrictions on the sample preparation process. If the percent transmittance of the strongest peak is less than 1% then the spectrum should be rejected. It it is less than 3%, then the operator should be issued a warning message. The strongest peak should also be less than 20%T. Additional information includes baseline values at 3,800 and 2,000 cm$^{-1}$ regardless of the mode of entry.

Following the generation and input of the peak table, as well as the input of other pertinent data which will be described more fully hereinafter, the operator pushes the INTRP button to initiate the possible structural unit (PSU) search routine. This routine, controlled by the data processing module 12, includes a series of automatically executed subroutines which adjust the data to a standardized format. First, the data is corrected for a sloping baseline. This subroutine is somewhat similar to the FLAT routine discussed hereinbefore.

In order to carry out the FLAT routine, the operator must enter baseline percent transmittance values for the particular spectrum at 3800 or 4000 cm$^{-1}$ and at 2000 cm$^{-1}$. If absorption bands occur at these frequencies they should be ignored and the most appropriate baseline value nearest to these frequencies used. These values are then used to describe a linear baseline in absorbance over the range of the spectrum and the percent T values (converted to absorbance) in the peak table are corrected by subtracting the calculated baseline absorbance at each peak frequency from the peak absorbance.

The next subroutine is a calibration routine wherein the data is corrected using calibration data entered by the operator. He must indicate whether he is using polystyrene or indene calibration data, and the system permits him to enter measured frequency values for the following peaks:

|  | IUPAC value |
|---|---|
| Indene | 3927 |
|  | 2305 |
|  | 1943 |
|  | 693 |
| Polystyrene | 3027 |
|  | 1944 |
|  | 907 |

The indene data will allow a shift and slope to be calculated by the data processing module 12 for correction of incoming data in both grating ranges. The polystyrene data will allow only a shift in the 4000 to 2000 cm$^{-1}$ region. This calibration data becomes part of the raw peak table and is stored with it. If frequency errors greater than 5 cm$^{-1}$ in the 2000 to 600 cm$^{-1}$ region and/or 10 cm$^{-1}$ in the 4000 to 2000 cm$^{-1}$ region are found, the operator is notified on the VDU and the option to continue with the routine is presented.

The third subroutine is a normalizing routine, wherein the data is normalized to selected peaks. The routine is somewhat similar to the ABEX routine described hereinbefore, except that the strongest peak i.e., lowest %T, in the spectrum outside the 3000 to 2830 cm$^{-1}$ region is located and a scaling factor is calculated on the basis of the absorbance of this peak such that the calculated absorbance for the strongest peak is set to 1.5. All other peak absorbance values in the peak table are then multiplied by the same factor and converted back to transmittance.

Next, the data is adjusted by deleting all the peaks having a transmittance greater than a threshold of the order of about 95% transmittance. This serves to reduce the affect of minor peaks. It is noted that the routine uses the intensity data, for the more significant peaks.

Next, the digitized, mathematically adjusted peak table of the unknown substance is examined to determine the principal functional groups, utilizing band matching techniques. In the computing apparatus memory there is a first library which includes of the order of about 850 structural units, such as for example ester carbonyl, aromatic amide, etc. in digitized form, stored in memory, and those that match with the unknown spectrum are displayed on the VDU screen. When all the functional groups have been tested against the unknown, the list of the identified functional groups are displayed, as shown in Table 1.

TABLE 1

| POSSIBLE STRUCTURAL UNITS: SHφφ5 | |
|---|---|
| 2φ2 | ALKYL GROUP - POSSIBLY METHYL SUBSTITUENT |
| 2φ4 | ALKYL GROUP GENERAL SUBSTITUENT (CONSULT MANUAL) |
| 212 | ALKYL GROUP - POSSIBLY HYDROXY OR AMINO COMPOUND |
| 5φ2 | ALIPHATIC ALCOHOL - PRIMARY OR SECONDARY HYDROXY GROUP (CONSULT MANUAL) |
| 511 | ALIPHATIC ALCOHOL - PRIMARY OR SECONDARY OR POSSIBLY CYCLIC HYDROXY |

In the table the serial numbers, for example 202, 204, 212 etc., refer to pages in an instruction manual which describe in detail the specific structural units enumerated. This interpretation takes about 12 to 15 seconds. It is noted that, while these interpretations are reasonably correct, there is always the possibility for error in a specific compound simply because of the complexity of the infrared spectrum introduced by the overlap of the bands.

Following the PSU search routine, the operator enters the library search routine, wherein the unknown is compared with the data in the library. In order to effect this routine, the operator pushes the SEARCH button and the input data of the unknown is processed in the data processing module 12. That is, the peak table is readjusted to a second preselected standardized format, whereby all transmittance peaks below a threshold of the order of about 85% transmittance are deleted. Next, the range is truncated. That is, the range is restricted to from about 1,624 to about 600 cm$^{-1}$ wavenumbers. The library disk contains files of reference spectra. Each spectrum is stored as a digitized peak table, with corresponding functional group data (structural units) to match the peak table. Thus, in addition to a band-to-band match, this system also matches the possible structure units (PSU's). That is, the file for each spectrum is in binary form and contains: several bits which indicate the presence or absence of preselected chemical functional groups (each group may contain one or more of the possible structural units described hereinbefore); several bits which indicate the state of the unknown, i.e., solid, gas or liquid; several bits which indicate the presence or absence of preselected non-organic elements; and a plurality of bits which correspond to the processed peak table of the unknown. About 27 seconds is consumed to make the comparison between the unknown and the known library of about 1,800 sets of spectra on one side of a disk. However, it is possible to search as many disks as the user has acquired. In the embodiment of the invention described, the search is actually four searches operating substantially in parallel. In one search the entire file for each spectrum is used for comparison or matching with the unknown. In the second search the bits in the file for each spectrum relating to the presence or absence of preselected chemical functional groups are excluded from the search. The third search is similar to the first search except that certain subsets of the bands of the peak table are omitted from consideration. This search, in effect, treats the unknown as a mixture. In this case, allowance must be made for the fact that the presence of a band in the mixture may be due to either component in the mixture. It is, therefore, necessary to not score the presence of a band in the mixture which does not appear in the library reference spectrum in the same way that the absence of a band in the mixture but which does occur in the library spectrum is scored. The fourth search is similar to the third search except that the bits in the file for each spectrum relating to the presence or absence of preselected chemical functional groups are excluded from the search. For example, the results of the first search described above are presented in Table 2.

TABLE 2

| NEAREST FIFTEEN SPECTRA FROM LIBRARY: SHφφ5 | |
|---|---|
| 9-6 | PROPYLENE GLYCOL NEAT |
| 9-5 | PROPYLENE GLYCOL |
| 9-4 | PROPYLENE GLYCOL CSPC623 |
| 9-3 | GLYCEROL NEAT |
| 9-2 | 1,2,3-PROPANETRIOL |
| 9-2 | 2-METHYL PENTANOL CSPC329 |
| 9-2 | 2,4-PENTANEDIOL, 2-METHYL- |
| 9-1 | N—BUTANOL 1φ% |
| 9-1 | ETHYLENE GLYCOL |
| 9-1 | ETHYLENE GLYCOL NEAT |
| 9-1 | PINE OIL CSPC425 |
| 9-1 | ETHANOL |
| 9-1 | SORBITOL |
| 9-1 | 2-PROPEN-1-OL, 3,3-DICHLORO- |
| 9-1 | BUTANOL, 3-METHYL- |

Referring to Table 2, the numbers associated with the library search are interpreted, as follows: the first number refers to the quality of the PSU match, while the second number refers to the quality of the band match. The numbers run from 0–9 where 0 is no match and 9 is a perfect match. Thus, even if the actual unknown is not contained in the library, the PSU match will indicate similar types of compounds, and the library search will indicate the closest 15 compounds contained therein with an indication of the quality of the match. Printouts for the other three searches are similar to Table 2.

It will be appreciated that the operator may add to this library or create his own library by carrying out exactly the same process of data acquisition and automatic processing as set forth hereinbefore in connection with an unknown sample, and then utilizing the storage routine by pressing the STORE button to place the known spectrum on a library disk.

Figure 5:
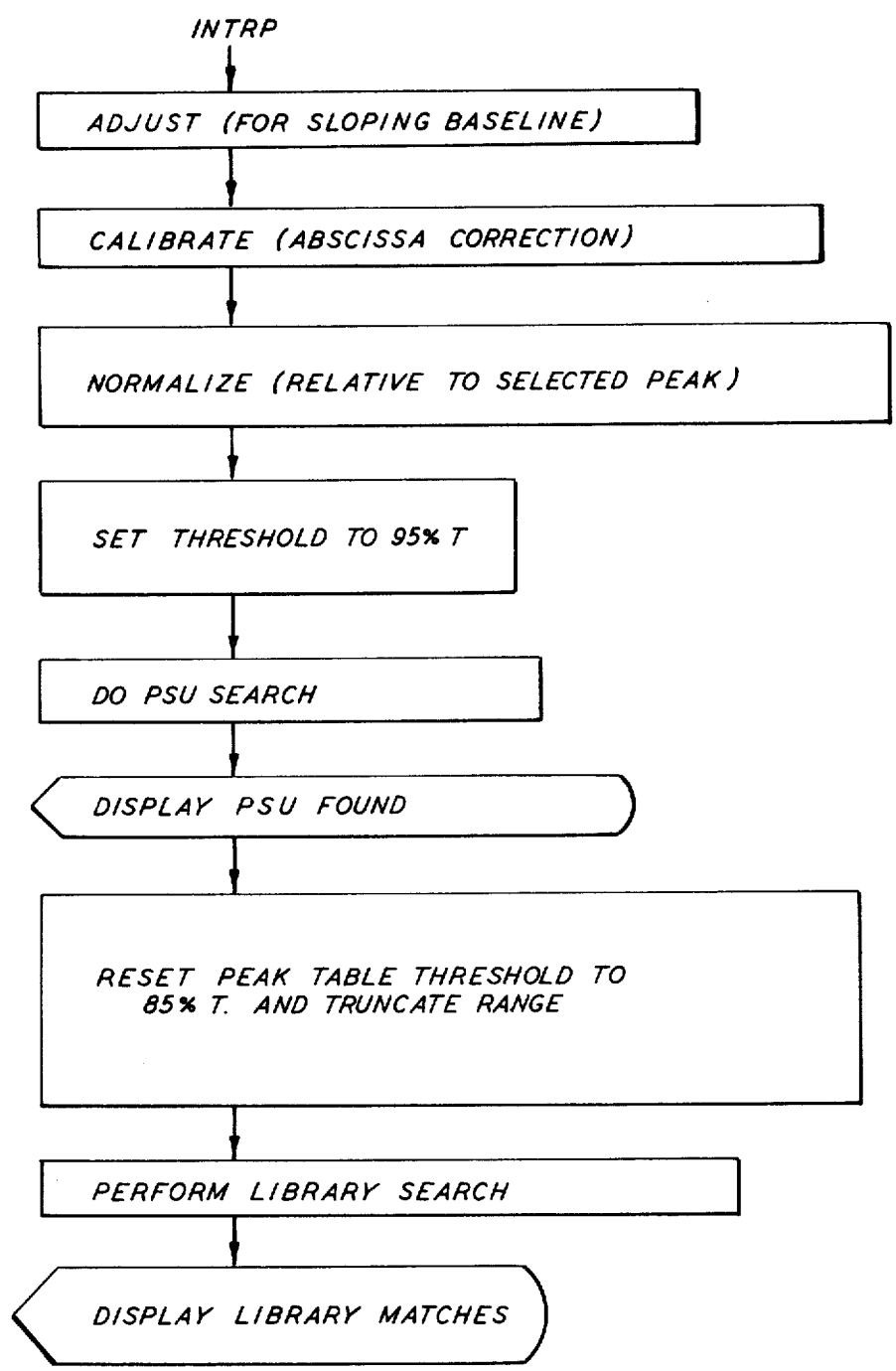
FIG. 5 is a flow chart of the application programs.

FIG. 5 is a flow chart of the application programs. Appendix A is a program for carrying out the basic operations of the system.

Although a certain particular embodiment of the invention has been herein disclosed for purposes of explanation, various modifications thereof, after study of the specification, will be apparent to those skilled in the art to which the invention pertains.

```
S11B10007E101A002E78000000000000000000002E78000000000000000E0
S11B10180000BD101F3F01CE79004FA70008BCBD7724F8CE0B22FFA1D2
S11B10300B9CE0BD4FFA104B4601B77B2A4FB77B29B7A0E48405B7A0FCA1
S11B1048B7A0FD8601B77A84CE0ED8FF7B27CE7A8C8414A70008BC7A84
S11B1060D324F8A700C604F77A85CE1A7DFF1587CE7A84FF1589CE15CC
S11B107887BDF83CBD3C17BD304BBD3C77FE79002703 7E14BD8400B7F2
S11B10907940402627CE1493FF15EACE1AC5FF15ECCE16F7FF15EECE28
S11B10A8172AFF15F0CE1734FF15F2CE1741FF15F47E11342B52810207
S11B10C02627CE1613FF15EACE164BFF15ECCE16F7FF15EECE1682FF61
S11B10D815F0CE1689FF15F2CE1741FF15F47E1134CE1754FF15EACE8E
S11B10F0187FF15ECCE17B9FF15EECE17ECFF15F0CE17F3FF15F2CE25
S11B110817FDFF15F47E1134CE182EFF15EACE1860FF15ECCE1897FF18
S11B11201 5EECE18 0DFF15F0CE1814FF15F2CE181EFF15F4BD1B5FBDB9
S11B11383A23BD3A31BD1B47866 5C6103F143F0DBD2D25BD3A31CE155D
S11B1150F6FF1587CEC788FF1589C60FCE1587BDF83CCE0001BD3A3E04
S11B11487FA0E47FA0E58602B77B25BD3A31FE15EAFF158BFF1587CE58
S11B1180C788FF1589CE1587C62FBDF83CFE7908270586 01B7A0F6BDDB
S11B11981CEEFE15F0FF158D7E14C4BD3A31FA0E47FA0E5FE15ECFF0A
S11B11B015BBFF1587CEC788FF1589CE1587C62FBDF83CFE79082705 33
S11B11C89601B7A0F6BD1CEEFE15F2FF158D7E14C4CE1700FF30CFBDD4
S11B11E02DFAC61ECE18FCBD1B04BD1B7EB6A0E4270F2B037E14BDB42F
S11B11F87B25810226A57E1148BD33C0240ABD1A837E11EABD1FFF244A
```

```
S11B1210 0FB47B2481 0327 0BB6 0A2B77B247E135ACE 0000FF79 007FA07D
S11B1228F77FA0E48601B77B25B47B2481 00 2703BD32EBB47B248 1031D
S11B1240 26124FB77B24CE19 1CFF158BBD1543CE19E92 0 0CFE15EEFFE2
S11B1258158BBD1543FE15F4FF158D7E14C44FCE1A4C20 0F8601B7A017
S11B1270F7CE1A6F2003CE1A5 38 40 1B77B2BBD1542CE1A21BD1591B69C
S11B1288A0E427 07810126 087E14BDFE79 0027 0BFE158BBC194E27 0830
S11B12A07E1220B47B2B265D7FA0F77FA0E4CE194EFF158BBD1543CEB3
S11B12B819F0FF158D7E14C4CE1A7B60 1B7A0F7200 3CE1A45B40220EF
S11B12D0 05CE1A45B403B77B2BBD15424FBD39 04F47901240BCE1A21E1
S11B12E8BD1591FE790 02709CE 0000FF79 007E12ABB6A0E427 0781 0178
S11B1300 26A67E14BDB47B2B8 10 12 6 05CE19B22 0 03CE1980FF158BBD2E
S11B1318 1543B47B2B8 10 12605CE1A0D2 003CE1A06FF158DB47994814D
S11B1330 0D27181592 75D814E26 0 37E11A37E14C4860 1B77B24CE1A69
S11B1348 5A7E1357 8600B77B24BD1605CE1A30BD1542BD1B47BD1B6FE1
S11B1360CE1A11BD1591BD3C17F6790 1270DBD1A83B47B248 1 0 227 0EFA
S11B1378 7E14E0B47B2481 0327 0A81 0 02 4 04BD1B477E11A8840 1B77B41
S11B1390 2 57E13FBB4FFB7A0FA8601BD3904FE79 0027 09CE 0000FF794A
S11B13A8 007E13D5B1 0 0272 0CE18CAFF158BBD15438 1 0D27 13819F2639
S11B13C0 037E14BD818F26 0 37E1305BD3B6 2 0C4BD3A31B6A0F7271101
S11B13D8B47B2B81 0 1 27 05CE1A7 6 2 0 12CE1A6F2 0 0DB47B2B810 12703D3
S11B13F0 7E12D1CE1A5 3 8 4 0 37E12D6CE1A3BBD15427E120CCE1A29BDB2
S11B1408 1542BD1605BD3C2EFE79 0 2 4 0 37E1 3BCCE 0 00 0FF79 0 0CE14BD
S11B14 2 0 42BD1B14CE1433BD1B14CE 0 0 01BD3A3E7E1168432F52205 4 4E
S11B14 3 8 4F20 4 3 4F4E5 4494E55450DCE1A37BD1542CE1A15BD1591F62E
S11B14 5 0 7 9 0127A7B47B2581 0 2 2 6 0 37E11487E11A3CE1A6BBD1542CEDB
S11B1468 1A25BD15917E144FCE1A1DBD1591B6A0E48101 2 7 4 07FA0E457
S11B1480 7E14E0B6 0 4B77B2BCE1A21BD1591B6A0E4810 1 2 7 2 87FA0E47D
S11B1498FE158DBC1A0 6 2 4 0 37E1305 7E14E0CE1A61BD1542CE1A19BDA0
S11B14B0 1591F4790 1 2 7 03BD1A837E14E0BD3A31BD1B4739B6799948130
S11B14C89F26 0 37E14BD8 10D27 0E162B0 22 0 0 6 8 47F811F233 ABD3B 6 4 67
S11B14E0CE 0 00 0FF79 0 0FE158BBD1543FE158BBC198 027 0BBC19B22764
S11B14F8 0 6FE158D7E14C4B799481 0D2 6 0 37E13948 15926 0 37E139415
S11B1510 81 4E26E5 7E11A381 1F23 0 37E14DD16FE158DA6 0 02787E10 0 6 3
S11B1528 27 0 608 0 9 087E1522C108240A86 02B17B2524 0 37E14E0EE01 51
S11B1540 6E 0 0FF1587FF158FBD3A31CEC788FF1589CE1587C607BDF815
S11B1558 3CCE18118 66 4C4 1C3F1539FF1587BD3A31CEC788FF1589CEA0
S11B1570 1587C62FBDF83CCE1 8 37 8 6 64C4 1C3F15CE 0 0 0 1BD3A3E39 0 6 3
S11B15 88 0 0 0 0 0 0 0 0 0 0 0 0 0 0 0 0 0 0 7F79 0 07F79 0 1FF15E2A6 0 0E4 01B11 5 0D
S11B15A0E4261 3F115E526 0EA6 0 2E6 03B115E4260 5F115E7272 2FE1542
S11B15B8E2EE 0 0FF15E4FE15E2EE 0 2FF15E6CE15E43F 0B240BBD1A83D6
S11B15D0BD3B664FB715E439CE 0 00 0FF79 0 0BD57 0 0390 0 0 0 0 0 0 0 0 0D6
S11B15E8 57 0 0 0 0 0 0 0 0 0 0 0 0 0 0 0 0 0 0 0 0 0 0 0 0 0 0 0 0 4 3 2F52 2 0544F2 0434F4E 09
S11B1600 54494E5 45CEB7E 0B620C4 05A7 0 0 85A24FA394B4559533A9B
S11B1618 8844495 2 8B41564552414745 2BF7204 4495 34B298020 20 2 059
S11B16 3 02 0 2020 20 2 02 02 02 02 020 20 20 2 02 02 02 02 020 20 2 02 0 2 0 2 09E
S11B1648 202020 4B4559533ABB444495 2BB5 2455054B8 41544552414748
S11B1660 45 2BF7 2 04 4495 34B29 8 02 020 2 02 020 20 20 2 020 2 020 2 020 20 54
S11B1678 20 2 02 02 020 202 02 02 00314A6 17 4610 0 03 14A60 813FB17E3
S11B169014610 0 4B4559533AB8444495 2BB4D414EB8 44495 34B8 02 02015
S11B16A8 202 020 20 20 20 2 02 02 020 20 2 02 020 20 20 2 02 020 20 2 02 02 02 6
S11B16C0 2 020 20 2 02 0 4B4559533ABB444495 2BB4D414EBB 44495 34B8 8F2
S11B16D852 455054802020202020202 020 2020 2020 2020 202020 20 2 0DB
S11B16F0 2 020 202 020 20 2 04B4559533AB853 415645B4 94E54525 0BB34
S11B17 08 5 0 4541 4B 4DB8 45444495 4B8 4F5 0 4494F4EB8 4D45 0B020E2
S11B17 20 2 02 020 20 202 020 20 2 0 03 14A6 0513 4C07 11D9 0 0 0314A6 0599
S11B17 38 1 34C0 7 11D9 08 13FB 0 0 0912660 12 7 60214700C134 10D11A374
```

```
S11B17501B126C004B4559533A8844495288494E5354802020202021
S11B176820202020202020202020202020202020202020202020265
S11B17802020202020204B4559533A8844495288494E53488524585
S11B1798505480202020202020202020202020202020202020202071
S11B17B02020202020202020204B4559533A8853415645884945420B
S11B17C850885045414B4D884F5044944F4E884D4958502020202098
S11B17E0202020202020202020202003144A041404000314A60414BF
S11B17F8040813FB000912460B127602147000D11A31B126C000314A60A
S11B181006144300314A60614430813FB000912460B127602147000D88
S11B182811A31B126C004B4559533A88444952884449475480202020EA
S11B18402020202020202020202020202020202020202020202020208C
S11B1858202020202020204B4559533A884449528844494754885200D
S11B18704550548020202020202020202020202020202020202020273
S11B188820202020202020202020202020204B4559533A88853415470
S11B18A04588494E545250885045414B4D884F5044944F4E884D495805
S11B18B8508020202020202020202020202020202020504C454153AF
S11B18D0452043484148474520404C494252415259204449534B2041EC2
S11B18E44204320F52202020202020202020202020202020504C41DF
S11B19004345205045414B204449534B204945204524495645201220F5
S11B191820202020204B4559533A8853415645884F5044944F4E802020E5
S11B193020202020202020202020202020202020202020202020209B
S11B194820202020204B4559533A88534154588534541524348880D0
S11B1960504541454D884F5044944F4E853544524584945853889634
S11B197840495850802020204B4559533A884F5044944F4E853544FE0
S11B19905245802044F5245284323F5229202020202020202020205C
S11B19A8202020202020204B4559533A884F5044944F4E80206C
S11B19C04D4F5245284323F522920202020202020202020202020E3
S11B19D82020202020202020202020202020200214700D11A3008C
S11B19F000214700A12CA0B12760D11A30E14831A12C01B126C00D11D3
S11B1A08A30E148300D011A30045444494544494475544344E545454341548
S11B1A20455352434841564524749454E53454525520D414E55414C20440DE
S11B1A38494749545A52524550445420534415242348820949454520C5
S11B1A50502020504541484D20204544444945420204444925202020057
S11B1A68415444552414745494958502020204D49585320202574340E
S11B1A80414C20F77901CE1700FF30CFBD2DFACE1AE3C41EBDF845F6C4
S11B1A987901B47900373F0033CEC7AEBDF8517FC7B1CEC7AFC617FF80
S11B1AB01B02CE1AE3FF1B0437CE1B02BDF83C33CB07B41AE3847FE78F
S11B1AC81AE3CE1ADC8A0AF71AD3A7005CBD1B04BD3A3139884552521A
S11B1AE04F5280000000000000000000000000000000000000000C9
S11B1AF8000000000000000000000007F1B7D7F46DBF744DCFF03
S11B1B046DD203286012006840220028603B71B7DFF46DD7F46DE7FD4
S11B1B2846DCE600C10426068101261220AC10D26068101260220076FA
S11B1B407C46DC0820E4B446D4CE46D93F1B846B7D270B81032707CECB
S11B1B58187BC60220A839B44D4CE44D53F12B44D4CA143F1539CE03
S11B1B700000B446D4CA1C3F1539390A0D00BD3A31CE1BD3FF1BE0CE1E
S11B1B88C788FF1BE2CE1BE0C60DBDF83CCE1B78644C41C3F15BD3A55
S11B1BA03B819F260484FF2006819F26048601B7A0E439811F2304817A
S11B1BB87F2306BD3B447E187ECE7994F5CC10727F1A600810D27E241
S11B1BD0820F2454E544522044494C452049440000000BD1B4784AF
S11B1BE864C6223F15CE0000FF30CFBD2DFAC60CCE1E4BBD1B06CE02DA
S11B1C0000FF30CFBD2DFACE1E46F67B26C1002703CE1E43FF8E24CE84
S11B1C181E5BBD1F80C423CE1E57BD1B04CE400B4794081012725B13E
S11B1C3002727FF30CFBD2DFACE1E49F6A0F6C1002703CE1E4AFF8EF7
S11B1C4824CE1E7BBD1F78C625CE1E7ABD1B04CE600FF30CFBD2DFABC
S11B1C60CE1F58F6A0FDE101270608080820F60808FF8E24CE1EA0FE
S11B1C78BD1F7CC625CE1E9FBD1B04CE080B4794081012704810222706
```

```
S11B1C90022003CE0600FF30CFBD2DFACE1E44F47B2AC1002703CE1EB9
S11B1CA843FF8E24CE1EC5BD1F80C623CE1EC4BD1B06B6794081012691
S11B1CC020CE0800FF30CFBD2DFACE7A8CFF8E24CE1EEEF47A84BD1F01
S11B1CD884C43ACE1EE7BD1B06B664C6A23F158664C6183F1539B6798F
S11B1CF040810127081022605CE1F352008CE1F212003CE1F44FF1F69
S11B1D0870BD1BE4FE1F70A602B71F737F1F72EE00FF30CFBD2DFAFE37
S11B1D201F72BD3A3E819F26037E1D92818F26037E1D92810D272781A8
S11B1D38C2272381C827AF81C1272681F7F2309847F811F23457E1D9E65
S11B1D50811F234AFE1F70808088EE004E00FE1F70860E5BDF807E1DF5
S11B1D6871FE1F70860E5BDF819A600810222037E1CEEF47940C102269B
S11B1D80078106230A7E1CEE810823037E1CEE7E1D06BD1B6739814EE5
S11B1D98270B8159270BBD3B6AFE1F707E1D06B6002002B601B77B26DA
S11B1DB07E1D5E814E2707814C27077E1D9EB600200286018760F67EF3
S11B1DC81DB08130272781312728CE7994E601C10D26C3C605CE1F58A6
S11B1DE0A10027095A271F08080808820F3E601F7A0FD7E1DB0CE7994A2
S11B1DF8A6017E1DDBCE7994A60181300270037E1D9EC6A07E1DEF814EF3
S11B1E02707815927077E1D9E8600200286018778A7E1DB0CE79949A
S11B1E28FF8E24C600A600810D27045C0820F6F77A84CE7A8CBD1F8A23
S11B1E407E1DB059455344F204E4C20202020204F5054494F4E53889F
S11B1E5820202082202050524494E5420415544404154494341404C1F
S11B1E705920285945532F4E4F29820822020205741564544E554D02
S11B1E884245522846290204F5220574156464C454E475448284C2988CE
S11B1EA0202082202050454148205044F5349454494F420544F045FA
S11B1EB8524144E4345202835302D313029882020208220204449535044CB
S11B1ED0415920404953542042F4A20505352028594F5532F4E4F2920E5
S11B1EE85743414C2088202020202020202020202020202020202020CF
S11B1F00202020202020202020202020202020202020202020202020C5
S11B1F1820202020202082020103196040101DE30401021DCAAC
S11B1F30080103E1E0E020103196040102DCA0A60103E1E02010321D5D
S11B1F48960401021DCA060103E1E080807321E2535053035360630A3FE
S11B1F60370730273808303839093039300A31300000000064322000EAC
S11B1F78C601200AC60220A0C603200204FF8E24CE8E24BDF8C3C95C
S11B1F9084FFB71FFA20037F1FFAFF1FFB5FCEB7C3E70008BCB7E0262D
S11B1FA8F8CE05FFFFFB7C1CEB7C3FF1FFBCE1FFBC60BBDF83CCEB7C387
S11B1FC0B4B7C13F12240139701DFFA2716CEA7716CFFA71CFFB7DACEAFA0
S11B1FD8C1FFA71ACE0800FFB7D839CE7B3AFFB7DA8A50B7E7D98A6D00D
S11B1FF0B7B7D739CEB7C13F1339000000007F22D2CE7B8AFF2263BC
S11B2008F22FF7F2302CE2131FF2303CEA12AFFA12B7FA12F7FA12741
S11B2020CE0FA0FF2300BD2467240372E2209BD23517C22FF7C22FFB6CE
S11B20387A362A037E20C3CE7993BDF80CA602EE008C524524048144A9
S11B205027037E20C38604BD344925678744E87F44E78D247E2255CFE2A
S11B2068A4E38C0FA02705B8C0ED8264FFFA0FE7C44E8BD24D4254FE82
S11B2080446FFA1027C44E8BD247E2536FE44E38C07D0262EFFA10095
S11B2098C46E8BD24D42523B6446E5B1A10227F02308FE44E5FFA10422
S11B20B02019FEA10220F6B644E6B1A10327E8B23F120E7BD22932403B27
S11B20C87E22098D2467240372E2209BD23517C22FFB47A362A06BD25F7
S11B20E03D7E2184CE7993BDF80CA602EA03EE008C57432408814126C
S11B20F804C14C27037E21707FA10A7F10FBB67A38B45CE7993BDFB87
S11B211000CA602EE008C494E263F81442438404B722FCBD344925485D
S11B2128B744E87F44E7CEA10A70A10A27020808FF22FDBD247E2530E5
S11B2140FE22FDB44E4F44E3A701E7007A22FC271708087C44E8202B
S11B2158DF8C504F2612814C260E7AA10A860320B7BD2C472502200824
S11B2170BD229324037E2209BD2467240372E2209BD23517C22FF5F7D51
S11B2188B7A352B75CE7A364D002A4E5CF17A352704080820F2B47A35BB
S11B21A0275F47255CCE0000FF44E77C44E8BD247E254EFE2300FA4402
S11B21B8E3B646E4BDF8212440FEA128E700A701F72300B72301080863
```

```
S11B21D0FFA1287C46E8BD24D425264D2703B722D2B646E6F646E5FE5E
S11B21E9A128E700A7010809FFA1287CA127B646E8B17A3526AD7E21B1
S11B22007BBD229325037E21787D23022624BD1B47BD1B4FCE7B3AFFA5
S11B2218A128B62264F62263BDF8212339BD1B14FEA1288450BDF90CAE
S11B223020E5CE18088664C41C15BD3A31CE2305FF2263CEC788FF22DE
S11B2248A5F4230258FB2302CB0DCE2243BDF83C4FB722D20D39BD2247
S11B2260C20C39000000000FE2238C8DFA2720CE7994FF2265CE2263CA
S11B2278C650BDF83CFE79948C454E240CB479968144260 5FE22630DA2
S11B2290390C397C23024FF622FFCE234EBDF851FE2303B6234FA70075
S11B22A8B62350A7018620A702B6230281082708080808FF2303C39E5
S11B22C00D39B622D22706CE22D3BD1B144FB722D239004341555449BD
S11B22D84F4E3A205045414B5320494E2052414E4745203330333302D28
S11B22F03238333020303C202E3120250D0000000000000000004C494EF5
S11B23094520455252 4F5253 3A202000000000000000000000000000FD
S11B2320000000000000000000000000000000000000000000000000A1
S11B233800000000000000000000000000000000000000000000000089
S11B2350000CE7994FF247ACE7A34FF247C9650A7004FB72473B7247178
S11B2368B72472FE247CE400F72475C64F0BBDF842FE247AB624752FCA
S11B23804FC60D4FE100270A084CB124752DF54A200E36C620E700087B
S11B23984CB124752DF7324CB724757D24752728FE247AFF24785FF7AF
S11B23B02476F72474FE247BB624724CB12475220FB72472A600B120A7
S11B23C8260C08FF247820EBB624717E246BF62472F72473A60081204 3
S11B23E0273B812C2737812F27337D2476 2B19B13A2A0491302A118189
S11B23F82E270B812B2709812D27058680B72476B624724CB12475225 4
S11B24100CB724727C247408FF247820BFB72477B624714C81272E3FC3
S11B24 28B72471 48FE247CBDF80CFA24737D24762601B0E700F6247415
S11B2440E701B24 7781 2F261 4B624714C81272E16B72 47 1B6 2472 A79B
S11B2458028601A703FE247808FF24787E23AEB6247140FE247CA701D8
S11B24 70390000000000000000000000000007DA0F62729BD255A002553
S11B2488 4D0 04 6E 7002547 7D25482468BD3D3F 0228255125 4D2549BD44
S11B24A03D3F03A025492553 44E32011BD25570044E30046E70025 47C6
S11B24B87D2548263FFE46E386A0C60FBDF821253386C8C600BDF8217F
S11B24D0222A0C39BD255E0044E50046E70025477D25482617FE46E50B
S11B24E884015FBDF81220F84E8C603BDF82125030C4F394F0D39F697
S11B25 0046E3B644E4FE2543BDF82122EFFE2545BDF8123E78401 0CBE
S11B2518390 07A25192 0037F2519CE0FA0FFA0FECE07D0FFA100CE03A6
S11B2530E8FFA102FFA1047D25192401 3984FFB7A0FB390BD60B0D003D
S11B254800000000000000002710008000004F2004 84FF2002B4 6011D
S11B25 60B7 2684BD3D4E267E26 8026 820000FE247E4F006F017D2684 1C
S11B2578 2A046F026F03FE26826F006F01CE7A34E6012A0150FE26802F
S11B2590A6012A037E2 6761123037E2 66 548CE7A34BDF80CA6002B03A8
S11B25 A87E2 66B40E401CE7993BDF80C7D26842A19FF25C9F72 685FE4F
S11B25C0267EFF25CFBD26BA000000002685000000397F2 6877F26888E
S11B25D8F72 6857F2 689A600812B 27 07812D26 077A2 6 89087A2 685FF67
S11B25F02 68AA600812E24187D26842B6E27548 4B1B72 684B6 24 58105
S11B26080222554A27 022014840FB72 68CFE 2687BD2 68D6 2468CBDF862
S11B2620 0CFF2 687FE 2 68A087A2 68526C27D2 68 42F 0B8481B72 68 47CDE
S11B2638 26854F20D3B62687F62 6897D26892A05405024014CFE267E94
S11B26 50A700E70139BD26 2DB62 68581012 60139 4FC60120098 4FFC6C9
S11B2668FE20034F4A16FE2 682A700E70139FE267E6F00E701390000E4
S11B26800000000000000000000000000000FF26B8782 6B8792 6B8B624D7
S11B26 98B8F42 6B9782 6B9792 6B8 782 6B9792 6B8FE 26B9 92 6B8B72 6EF
S11B26B0B8F72 6B9FE2 6B83900 0 00BD3D 4E2 7B027B227B400 007F27AE 44
S11B26C8CE0000FF27A2FF27A4FF27A6FF27A8FE27B2A600B727AF26CC
S11B26E0037E2774FE27B0A60081 2B2707812D260C7A27AE0BFF27B060
S11B26F87A27AF2777A600812E272C840FB7279 0BD2790BD3D3F01A8CC
```

```
S11B2710027A227AA27A2BD3D3F03A827A2279E27A2FE27B00BFF27B05C
S11B2728FA27AF274720CE7A27AF2740B627B0F627B1FB27AFB900B7C6
S11B274027B0F727B1FE27B0A600B40FB7279DBD2790BD3D3F03A827CF
S11B2758A6279E27A6BD3D3F02A827A627AA27A6FE27B009FF27B07B1
S11B277027AF26D4BD3D3F03AC27A427A227B47D27AE270BBD3D3F0067
S11B2788FC27B427B427B439BD3D3F05BB279E279C002639000000000C2
S11B27A000000000000000000001A00000000000000000000000000007C
S11B27B0000000000000000000000000000000000000000027CEFF000011
S11B27D00102030304050606070809090A0B7F7934F2AE6A26E29E5B60
S11B27E817D38F4B07C4803CFFFD22446B90B5DAFE23484D92B6DB00A3
S11B2800254AFFEE7B000010751FF82EA53C9249D0567062B14E0F79F0
S11B281823B3C98E0797E4A16CAAA0B387BC25F15900000F8B20083174
S11B2830B5441257BF4C9F82C29A3EB327CD93E99B07525F200AC6020F
S11B28482006C6042002C60630EE00A600EE01482A02EE00FF27B63075
S11B28600EE00A603EE04482A02EE00FF27BB72875CE2B78EE006E0035
S11B2878289028BA28C4294F8A06B727C77F27BA20058601B727BAFEB3
S11B289027B4E601A6002B06261CC10A24185F7D27BA260B8604B727F0
S11B28A8C77F27C5B67D7E2B1D867D7E2A85CEFFFE0B584924FBFF2730
S11B28C0BB7E29AC84FFB727BAFE27B64FE6005846B727C5572B644F4B
S11B28D85749B727C8B4021029B5FB727C7EA03F727C6EA02A6017D27D7
S11B28F0C8241CE0004445A7A27C6092B6F824097C27C62604CB0189BD
S11B290800CE00007A27C72B1BFE27C6F727C6164F20F1FF27C72A09D5
S11B29207C27C62604CB018900FE27C52A3C43537027C62635CB0189C0
S11B293800202FB64EC62020084F5F7D27C52704B67FC4FF7E2A85B690
S11B2950FFB727BAFE27B64B09B727C5B727C6EA01A60047547627C697
S11B296824F9F727BFCE27CC08A1002EFB2D11E11222F527022309307F2
S11B2980F627C6E1243322EBFF27BBB627BBF427BCF027CCB227CB2518
S11B2998A8C10F2EA4CB02F727C8A612E624F027C6B227BFB727BBB4D2
S11B29B00F8A1047542A4FC5949B727C3F727C4B727BFF727C0C410B679
S11B29C827BB485924FC5BCE2803B627BA2A03CE2827BD2B79A602B75F
S11B29E027BDE603F727BEE001A200B727C1F727C2A604E605F027BEC4
S11B29F8B227BDB727C5F727C4FB27C2B927C1B727C9F727CAB627BAFB
S11B2A102B0EB6A27C1F627C2F027C6B227C5200CB627C5F627C6F027B1
S11B2A28C2B227C15B49B727C1F727C2BD2B35B627C9F627CA7D27BA0E
S11B2A402B08F027C6B227C52006FB27C6B927C5F727C2B727C1FE2775
S11B2A58BFFF27C3B02B35FB27BEB927BDF727C4B727C57D27BA2A1FF2
S11B2A707F27C7FE27C70D462001445609F26FB2404CB018900FE27B85F
S11B2A88A700E7017E2B2EF627BCCE27CEBD2B78A600B727C8A612E6E6
S11B2AA024F027C6B227C52403F7A27C87D27BA271FCE00047727C846C9
S11B2AB5409F26F82404CB018900D4D2AC07D27C82BBB847FC6FF20B5E0
S11B2AD07D27C92A0F53437327C8CB018900240327C90D7627C77F74
S11B2AE827C5FE27C67D27C8270BF727C516B627C80B0B200F4D260C01
S11B2B005D26057F27C720151759F0909810F220A8A10782TC5594924B7
S11B2B18F909FF27C6FE27B8A701E702B427C7F627C5A700E70330EE10
S11B2B30003131AE064FF627C32609F627C4F727C35F20205F0D7627EB
S11B2B48C42406F827C2B927C14567A27C426F1200A2406F827C2B9FB
S11B2B6027C1456A7A27C326F1445624048CB018900B727C5F727C63BB9
S11B2B78FF27C1F827C22403F7C27C1F727C2FE27C1397FA0F97DA0FBBC
S11B2B90270139BD2C4ECEFFFFFF2D1CB6A127B72D1BCEA12AFFA1289F
S11B2BA8EE00FF2D1F7D2D1D272884D0C407B0F82122A4C7DA10A2A0306
S11B2BC07E2C217D2D1C27127F2D1CBD324B002D01002D0F002CFF0098
S11B2BD82D00BD032A5002D1F002D21BD3D3F04102D1F2D212D1FFEA1A7
S11B2BF028B62D20F62D1FA701E707A2D1B274608080B7E2BA57FB1
S11B2C082D1D7DA10A2B26BD324B002D05002D13002D03002D117E2B2A
S11B2C20DA7D2D1C27BDB62D10F62D0FFE2D21A701E70020AEBD324B0C
S11B2C38002D0BB002D13002D09002D1120943986FFB72D1E20067F2D4E
```

```
S11B2C501E7E2CA8CEA10AFF2D15CE2D0DFF2D177DA10A2A08CE2D0599
S11B2C68FF2D19201CCE2CFFFF2D19FE2D15E600A601FE2D19EE00BDD5
S11B2C80F81EFE2D17E700A701FE2D158CA11027170808FF2D15FE2D1A
S11B2C98190808FF2D19FE2D170808FF2D1720CB7DA10A2605CE2D0DD7
S11B2CB02003CE2D0FFF2D17A601E6002A02405326398C2D11271B8C55
S11B2CC82D1327147D2D1E260B810A231CC6FFF7A0F9202181142218B48
S11B2CE0200F7D2D1E2604810522EA2004810A220A8C2D13270708083E
S11B2CF87E2CB50D390C390F570901079702B50BD307980388000000004
S11B2D100000000000000000000000000000000002D230000CE000188
S11B2D28FF30CF8464C6163F15B603B730CEBD2DFAC64FCE2E07BD1B65
S11B2D40047A30CE26F0BD2DFAC64FCE2E56BD1B06BD2DFAC64FCE2EC5
S11B2D58A5BD1B06BD2DFAC64FCE2EF4BD1B06BD2DFAC64FCE2EF4BD6F
S11B2D701B06BD2DFAC64FCE2F43BD1B068603B730CEBD2DFAC64FCE0A
S11B2D882F92BD1B067A30CE26F0BD2DFAC64FCE2FE1BD1B06BD2DFA69
S11B2DA0C44FCE2E56BD1B06BD2DFAC64FCE2E56BD1B06BD2DFAC64FE0
S11B2DB8CE3030BD1B068603B730CEBD2DFAC64FCE2E56BD1B067A30E2
S11B2DD0CE26F0BD2DFAC64FCE307FBD1B068603B730CEBD2DFAC64F78
S11B2DE8CE2E07BD1B067A30CE26F08464C6183F1539FE30CF8464C65E
S11B2E001C3F157C30CF392A2A2A2A2A2A2A2A2A2A2A2A2A2A2A2A2AC8
S11B2E182A2A2A2A2A2A2A2A2A2A2A2A2A2A2A2A2A2A2A2A2A2A2A2AAE
S11B2E302A2A2A2A2A2A2A2A2A2A2A2A2A2A2A2A2A2A2A2A2A2A2A2A94
S11B2E482A2A2A2A2A2A2A2A2A2A2A0D0A2A2A2A2A2A2020202020200ED
S11B2E602020202020202020202020202020202020202020202020202054
S11B2E782020202020202020202020202020202020202020202020203E
S11B2E902020202020202020202020202A2A2A2A2A0D0A2A2A2A2AFF
S11B2EA82A2A20202020202020202020202020202020205050506A
S11B2EC05050502020202020202020202020202020454545454545AD
S11B2ED8454520202020202020202020202020202202A2A2A76
S11B2EF02A2A0D0A2A2A2A2A2A2A202020202020202020202020202020A9
S11B2F0820202020502020202020502020202020202020202020204D
S11B2F202020452020202020202020202020202020202020202070
S11B2F382020202A2A2A2A2A0D0A2A2A2A2A2A2020202020202020202042
S11B2F502020202020202020202050505050505020202020202045
S11B2F682020202020202020204545454520202020202020202020B9
S11B2F802020202020202020202A2A2A2A2A0D0A2A2A2A2A2A20FA
S11B2F98202020202020202020202020202020205020202020200ED
S11B2FB0202020202020202020202020202045202020202020200E0
S11B2FC82020202020202020202020202020202020202A2A2A2A2A0DCE
S11B2FE00A2A2A2A2A2A200A2020202020202020202020202020200B9
S11B2FF820502020202020202020202020202020202020202020204568
S11B3010454545454545202020202020202020202020202020202020C6
S11B30282A2A2A2A2A0D0A2A2A2A2A2A202020202020205345415243B3
S11B3040482020202053454152434820202020534541524348202060
S11B305820534541524348202020205345415243482020202053454150F7
S11B3070524348202020202020A2A2A2A2A0D0A2A2A2A2A2A20204F3A
S11B308850595249474854203139373920544845205045524D49442DF4
S11B30A0454C4D455220434F52504F5241544F4E2020564552534966
S11B30B84F4E20412043454F564542425220202A2A2A2A2A0D0A000057
S11B30D000BD3D4E6343229000FE3229FF322BCEA60CFF322DC628E4
S11B30E8CE322BBDF83CBD3D3F0228A61A3212A634C462CE3216B46D3
S11B310001D47240506644CE321AFFA63AF73164BD3D3F0238A61EA63AB0
S11B3118A63CBD3D3F0238A620A63AA440B6A624B7A61A7FA624BD3489
S11B3130C50079E400A61400A61600A61880A63480A63C80A644000A663
S11B314824403229FE314F31517E3175020204050405080120404062E
S11B316042090206000A00020E080241430402020905050000010101013A
S11B317801CE583AFF79E4F6A61CCE321EFFA644CE7A0C8654A700FFEB
```

```
S11B3190A446FEA644A6000BFFA644FEA64674A61C76A61D2402A70092
S11B31A80B9C7A1626E17DA61A270B8653A700B6A61A8B30A7010B59B9
S11B31C02A048656A703B6A62526086F026F036F046F05CE79E4F6A6FF
S11B31D82627339644453270286E3A73EC642E73FB6A6275F47594759D7
S11B31F02704CB40E73DC64DE73AC6204D26028623810A2603C6314F37
S11B32088B30E73BA73CBD1B1839026400002CB000004271000412DF5
S11B322044462020202020200000000A60C00800000000000000F6
S11B3238000000000000000000000000000000000BD3D4E3233CD
S11B32503235323732390000FE3233EE00FF3233FE3235EE00FF3235B9
S11B3268FE3237EE00FF3237FE3239EE00FF3239BD3D3F0400323932F2
S11B328035323FBD3D3F05B83243323F323FBD3D3F0400323732333232
S11B32983FBD3D3F02B83243323F323B39BD3D4E3247324900D0FE3220
S11B32B047EE00FF3247FE3249EE00FF3249BD3D3F0400324732333227
S11B32C83FBD3D3F01B8323F323B323FBD3D3F03B8323F3235323FBD30
S11B32E03D3F03A4323F322F3249398618B733B57F339FCE33B88469F3
S11B32F83F12256DCE100FC6123F158469D4C03F144F5F9D47FF33B65C
S11B3310C450FF33A3BDF80909A600B1002704B12026A6095A26F22035
S11B33281DF733A2FF33A58462D5A2709096D0024F8A7002DF48469CE8D
S11B3340D339F3F1825238469CE33AB3F1B251A7A33B52718FE33B486C1
S11B3358508DF80C8CC78026D3CEC000FF33B420A7F77901CE33BC845B
S11B3370493F1339C11B2709F8C939C11B2D02C01B8733BE58175858A0
S11B33881B5F48594859485988338EC9C0B733BFF733BEFE33BE3900DE
S11B33A0A000000000000000D0A000000D233A933AA0000000000035
S11B33B850524E5449FF0000CE7994FF3445C405A6008100270652A274D
S11B33D000C820F44FA7005A27030820F8C605CE343EFF3447CE344553
S11B33E8BDF83CCE343EFF3445CEB7E0FF3447CE3445C405BDF83CCE70
S11B3400D343A8D1F972522BD342AB6B7C1CEB7D63F17250DFEB7DAC607
S11B3418508DF809FFB7DA20E9C11724D4BD1FF40C39CE7E3AB620A70A
S11B3430008C8DF92703D820F4394D4444310000000000504B0000004A
S11B3448008734827D7A352B2FC6014FCE7A366D002B0F4D2707B134DA
S11B3460B2261D2006F73483200140F17A3527D55C080820E2B13482A9
S11B34782606B434834C0C390D39000000000000000000000000000C8
S11B34900000000000000000000000000000000000000000000020
S11B34AB00000000000000000000000000000000000000000000008
S11B34C00000000007F34848AFF873485201186012002B4FFB73484F4
S11B34D82003F73A847F348530EE00FF348F5FF734EBAB00C803B1FEFE
S11B34F02AF5C002F734F8EE00EE0008FF349BCE04F7361B7F3484CE00
S11B350879E4B4348527D3BD3972FF3491FF349DCE349EFF349FFE3412
S11B35208BFF348DFE348D0B08FF348DA600E60148B7353947CE353C35
S11B3538EE00AE0035522564D3583359136443593464346459F35B322
S11B3550035CBFE348BFF348DFE348FA6008D1CE2605B4348426D784FFDF
S11B3568B73487201370348786D20FE349DA70008FF349D634852BA43B
S11B35807E35E18426DFE349DA700085A26FAFF349D2091F73489BD38D3
S11B3598DBFF349B7E37ECFE348D0B08FF349BCE349B8DF83CFE349BA8
S11B35B07E3529FE349F0B0B08FF349FE700B6348DF634B8EA01E702C1
S11B35C87E3524FE349F6AD02707EE01FF348D20EF090909FF349F20DC
S11B35E0E7FE349D8604A700B634B52623FE3491FF349DB43484B101AD
S11B35F8204BD1B107E3415B434876434B4270B5D1B142003BD1B18C6
S11B3610B6348727B330EE0031316E007A2AF31E7B1AD7F37C1DC6F807
S11B362B7CA7C5AC7D46D89C7E41B9377F2BF5C30019999A0110000D4B
S11B3640010000002400000033B80000427100051B4A0005F42400C7
S11B3658069894B0075F5E103FFF00008004B7348A2A09F7348977348FB
S11B3470C2DC20181784DFB734C2C4F0CA085424FD1BB734897D348ACC
S11B3488270D2004CE34B4095A24FCFF349BCE34AAB4F0C41A700088B3
S11B34A0C10F26014F5A26F57F34C07F34C17F3497BD3808A600E60198
S11B34B8EE027D348826D3BD43B9FF3499F73498274048240D37A34C117
```

```
S11B36D047B7349786F7B734C0CE361CFF36E6BD38A2B0349780000050
S11B36E8200F000000FE36E4080808087C34C020E3FE36E4FF37046BDD7
S11B37003D3F02AB3497000349786434C2F6348A2E03BB34C0CE34B3FC
S11B371B084A2AFCFF36E6CE34B3B602B734C4F6349AF734C3F63499A1
S11B3730B634987834C3594969007A34C42B1C26F237F634C3FB349AC3
S11B3748F7349AF734C333F93499B9349824DC6C0020D878349AB7349F
S11B37609BF734990BEC34E424B84D2A1AC60A20086C00E1002E056FBB
S11B3778000920F58C34B22606BD37F87C34C0B6348A2F1EFE36E484BC
S11B379045A700862BC630E702F634C02A0350862DCB30A701E7037F7B
S11B37A834C0B634C02A0FBD37F8FE36E40BFF36E7C34C024F184F008
S11B37C07D34C1270286FDB734B2B434C04CB737D7C62ECE34AAA60031
S11B37D8BB30A700BC34B326057A37D7E70008BC36E624EAF63489CEF5
S11B37F0349BBDF83C7E3524FE36E6A600A701098C34B126F66F01397F
S11B3808B634B62630BD38724D2F08B7348731317E35E1B734885D2794
S11B38201BFF36E6BD3857B7349F3F73494BD3857B73495F73494FE340E
S11B3838937A348639FE3493BC349526057F34B620BE08087D34B82778
S11B3850020808FF349339BD3872A600E601C00182005B497D34B82713
S11B3868025849FB36E7B936E439FE348F8601E400C1BD240508080B8C
S11B388020F5C1FE27144F58460808088FF348F0909EE00582402EE00EA
S11B3898C40439000000000000030EE00A600EE01482A02EE00FF38C7
S11B38B09B30EE00A603EE04482A02EE00FF389DFE389BA600E601F71D
S11B38C8389FEE02FF38A0FE389E6004858112E212D1BF6389FE10196
S11B38E0221B2612F638A0E10222OF2609F638A1E1032206270484048B7
S11B38F82002840BB7390530EE0031316E00B73A22FE3A1AFF3974FE0F
S11B39103A1CFF3976CE0000FF3978CE3974B4003F12253BCEFFFFFF9C
S11B39283972CE396A86003F17252CFE3984B43A222405FF3A1E2008C3
S11B3940BC3A1E27037E3958FE3986402405FF3A20200FBC3A20270321
S11B39584F200786012003BD1AB3CE39683F133900FF0000080398843
S11B397000000000000000000000000000000000000000000000000038
S11B398800000000000000000000000000000000000000000000000023
S11B39A000000000000000000000000000000000000000000000000008
S11B39B800000000000000000000000000000000000000000000000F3
S11B39D000000000000000000000000000000000000000000000000D8
S11B39E8000000000000000000000000000000000000000000000000C3
S11B3A00000000000000000000000000000000000000000000000000AA
S11B3A18000040464431000000000086465CE3BFF3F128465C4443F14FE
S11B3A3039CEC788C6434FBDF84239CE004EFF3C0FCE3B95FF3C114FFD
S11B3A48A70008A7008C3BE526F8B73EE7B73BE8CE3C0D8A653F17A691
S11B3A6007E604FE3C11BDF81EBB3BE8813C10230CBD3B44F43C10F79B
S11B3A783BE87E3AE7B73BE84ACE3B95BDF80CA60081 0D275A911F2375
S11B3A90048 17F2352CE3BE9A100271008080 8E600C100273CA10027ED
S11B3AA8037E3A9C08EE006E00CE001BD3B4D7E3A58FE3BE7BD3B4D7E
S11B3AC07F3BE87E3A58B643BE84A27E5CE0002BD3B4D7E3A58BD32EBEA
S11B3AD8CE0001BD3B4D7E3A58CE7994A70039F43BE8CE3B95FF3BFBE7
S11B3AF0CE7994FF3BFDCE3BFBBDF83CCE7994A60039FF3BFBCE0F06E1
S11B3B083F0C5D2720BD3B5B09FF3BFBD3B5F8A00BD3BBAFE3BFDBDD0
S11B3B203B5FFE3BFB09272FFF3BFB20E0BD3B58FF3BFD8A00BD3B8A98
S11B3B38BD3B5809FF3BFDBD3B5FFE3BFB09270FFF3BFB7A3BFEFE3BF6
S11B3B50FDBD3B5F7E3B3239B464C61A3F1539B464C61C3F15398 46545
S11B3B68C60A3F0939FF3BF9BD3B02FE3BF97A3BE8924FAFE3C13F4B2
S11B3B803BFA095A26FCFF3C1139B73BE6B464CE3C033F18390000000B
S11B3B9800000000000000000000000000000000000000000000000011
S11B3BB00000000000000000000000000000000000000000000000F9
S11B3BC8000000000000000000000000000000000000000000000E1
S11B3BE00000000000000000C93ABA083AC6803AD58F3AE19F3AE111
S11B3BF80000000000004B45594200D00013BE40000000000000D004A
```

```
S11B3C1050000000000000CE0000FF7902CE3C233F053981BB2606CE20
S11B3C28FFFFFF79023BCE0000FF7900CE3C67BD1591FE79002607CE41
S11B3C403C6BBD1591398CFFFF2605CE3C6F2013B47901CE570208E67F
S11B3C5800C1FF2709C47F1126F408BD1B14395343202050452020B892
S11B3C7042524541EB00D7FC8037FC8027FC8067FC8077FC80B7FC87F
S11B3C880A7FC80086 1FB7C90984FFB7C801B7C804B7C805B7C80B86B9
S11B3CA004B7C803B7C802B7C806B7C807B7C80BB7C80A8603B7C80BD3
S11B3CB86C80984E081A024157E3CD50F8455B7C93B6DA807FC93BE8
S11B3CD00E1802601 39BD1B5FBD3A31CE3CF6FF3CF2C61DCEC730FF34
S11B3CE83CF4CE3CF2BDF83C3F01000000053595354454D20494E5473
S11B3D0045524C4F434B2C20534545204D414E5414C0D00000000000D3
S11B3D18000000000000000000000000000000000000000000000000 BF
S11B3D30000000000000000000000000000000000007B3B7B3D897B3DD8A5
S11B3D487E41897E3D517E421ECE3D2E4FA700088C3D3F26F8392A2A43
S11B3D602A45584543555494F4E2054494D45204552524F5220232000D
S11B3D78200DCE3D77A700E701CE3D5EBD1B143F0130EE00FF3D22A63A
S11B3D9000EE018540 2702EE00A6002B2D2604A601271CFE3D22EE03EC
S11B3DA8270AFE3D22080808082007FE3D22EE09EE0031314E00FE12
S11B3DC03D226D0326E7EE0720EFFE3D22EE0326EAFE3D22EE0520E158
S11B3DD830EE00FF3D225F8A6BE3D23F93D2230E700A701FE3D22A633
S11B3DF00344EE02240309EE00A600E601FE3D22EE04FF3D13EE01EB5D
S11B3E0801A900B73D15F73D16FE3D22A60144EE00240309EE00A600A7
S11B3E20B13D152E0B2D17A601B3D162402200EF63D13B63D1430E7A3
S11B3E3800A701FE3D1539BF3D2430EE00FF3D22A60027108 1042E0C05
S11B3E50E601F73D27C4A8271B7E42795F81062F10B00481052601 4C8E
S11B3E6881092F058009168604B73D27F73D26A601EE02B5402702EE6F
S11B3E8000FF3D28FE3D22EE0485102702EE00FF3D2AFE3D22EE0685BB
S11B3E98042702EE00FF3D2C84A8B73D3E2778FE3D22A60081052616C9
S11B3EB0FE3D28FF3D2CFE3D2AFF3D28B63D3E4B4984B1B73D3EFE3D2E
S11B3EC828A600E601EE02F73D1AC680F43D3E2409F63D1AED43B9F70A
S11B3EE03D1AFF3D1BB73D19B63D27272A81082C04B1042E22FE3D2AAD
S11B3EF8A400E601EE02F73D1FC420F43D3E2409F63D1FBD43B9F73D1B
S11B3F101FFF3D20B73D1EB63D27CE40722006B63D27CE3F314D270577
S11B3F2808084A26FBEE006E003F6E3FC140093F993FA93F893EA73F04
S11B3F40553F423F6843538900C90039FE3D28A600FE3D2A398DF5433B
S11B3F585F48B601240 2BDE5201 68DEBAA0020F08DE2A4002 0EAFE3DCA
S11B3F7028E600A601BD3F45FE3D2CE700A701BE3D24FE3D2231316EFD
S11B3F8808FE3D2AE600A601FE3D28E700A70120E6FE3D28A601E6003B
S11B3FA0FE3D2AAB01E90020CFFE3D28E600A601FE3D2AA001E2007DC7
S11B3FB8 3D2427BCBD40492097BD3FE33048596801690024048B04E968
S11B3FD0036A0626F036A602A805322A03BD3F457E3F78B6 1036FE3DE5
S11B3FE82AA601E600372A03BD3F453637FE3D28A601E600372A03BDE3
S11B40003F453637 30EE076E00BD3FE33086014D032B04C68046903C0
S11B4018 2B04B1112 6F5A706AA601E600 6F006F01A004E20324078B0434
S11B4030E9030C2010D69014900640 36A046A0624E6E600A6017E3FE4
S11B4048D54D2702CA01B43D26CE40 65084A2EFC5D07840CA100270570
S11B4060A1062701433904000404 0800040808000800 40A240AC40B00B
S11B4078408440B84127412E408640924 09AB63D1943BD417C4D2B12A4
S11B4090203BB63D19BA3D1E20F0B63D19B43D1E20E8B63D1988B8B797
S11B40A83D1920248601200A86022006B603200286048B4BB63D2627B9
S11B40C00FF63D19B63D1A2702CA01BD40492 0BAB63D3EB4082617CEA0
S11B40D83D19680073D1767006A601E02BD437C3714327E3F78FE3DE3
S11B40F02CF63D1BB63D1CE702A703F63D19B63D1A7E3F78C6A8F73D6B
S11B41 0927FE3D22FF3D13CE4118FF3D22BD427900003D193D1E3D19C4
S11B4120FE3D13FF3D2239B63D3EB40120A7FE3D19FF3D1EFE3D1BFF1E
S11B4138B3D20FE3D2AEE0026048D39208BFF3D2AB63D2A2B0FFE3D2AFE
S11B4150 09FF3D2A27ED860 18DAA20F1FE3D2A08FF3D2A270686018DED
S11B4168BD20F1FE3D19FF3D1EFE3D1BFF3D20BD037E40B0CE0110FF52
S11B41803D197F3D1B7F3D1C3920EE00FF3D1BB603B73D3BA604B73D25
```

```
S11B419839A600E601EE02FF3D2EEB01A9003637FF3D30EE042746FF1F
S11B41B03D36FE3D13A60644EE052722240309EE00EE00092718FF3D76
S11B41C832B03E3F01003D323D363D343332FB3D35B93D3420023332989
S11B41E0FE3D13080BFF3D137A3D38270DFE3D3008087E41A67F3D381F
S11B41F83332FE3D39A700E701FE3D2EE001A2002B0DE003A2022A0768
S11B4210FE3D1331316E058642C6307E3D7A30EE00FF3D3A30EE02FFC9
S11B42283D3CE600A601C4402705EE01A60009E402FE3D3AEE0027151F
S11B4240A700E701FE3D3A0809FF3D3AFE3D3C0808087E42273131B64A
S11B42583D3CF63D3D30A700E701FE3D3A6E02000000000000000000BD
S11B42700000000000000000036B63D27FE3D22EE024848402EE00F1
S11B42898836A600E601EE0236B63D2748322503BD43B974247F74268B
S11B42A0FF4269FE3D22EE04324848402EE003A4A600E601EE0236B494
S11B42B83D2784203226030BD43B9B7426CF7426DFF426EFE3D22EE06C3
S11B42D03249482402EE00FF427733C10127037E44BF84247B73D1768
S11B42E8B64267F6426C48581B47B742714F5F874274CE424F0D66003E
S11B43002411377F64274FB8426AF7427433F94269B9426B465474427433
S11B431B764275640026E1098C426C26D8810F221A4D26087F42717FB8
S11B43303D17200F7A42718A10784275794274594924F636B63D278439
S11B434808260F32CE42718D2BFE4277A700E701201B32784271783D1E
S11B4346017764271FE4277A701E702B64271F64274A700E703FE3D22B4
S11B437831316E0836A4002E04314F5F39B1052D0731C6FF867F201D39
S11B4390404C6F004725024A004A322602164F6D002708C4F0CA084454B9
S11B43A824FC4D2B0D7D3D172A064353CB018900397F3D17CE00044D4D
S11B43C02A097A3D174353CB01B900260C172406CE00004F5F390909B9
S11B43D85F810F2207098A10584924FCFF3D15F73D1516B63D167D3DDA
S11B43F01727028A807F3D16FE3D15397D42752A237C4274261E7C4257
S11B440B73241970427226148610B742725FB44271485B4B8E0229555B9B1
S11B442046B742718B3D27840B26127842717A3D17774271B4272F473
S11B4443B4273B7E434CB64272F642737E434429160C461B74271CE4246
S11B44507180845B67D42762A37C4271209E2A1C36B6427285F0322688
S11B4446B0BB1B02607B63FB7427620D6C480CA3F86FF20025F4FB7423A
S11B44B072E7427B37427477F4275F7427120CD7F42757F426B7F427075
S11B44998C102260337E461537CE4267BD45B4CE426CBD45B68608B74222
S11B44B076B6426748F6426C587A42762D3911273A2E0C8D168D148DC2
S11B44C128D10BB0220EA8D188D16B0D148D12CB0220DE0C744268749D
S11B44E0424976426A7426B390C74426D74426E74426F744270391147
S11B44F82E0117B742718D0BB0DE7B642672A06CE4267BD45EE6426CC2
S11B45102A06CE426CBD45EE3281032670B6426BB84270B74275B4427I
S11B45284A89426FB74274B4426B94926EB7427B364268F9426D281F71
S11B4540B60456200157764273764274764275A426F37C42717C4271C2
S11B455828055956E4474F742725D0C2A09CE4271BD45EE0D29EC76E5
S11B4570427179427579427479427379427286427285F02605CE427137
S11B4588B8D2C7E43FCB6426B8B40427B87427B8B4426AB42426FB74274B4
S11B45A04249B2426EB74273F64268F2426D25030D208B0C208BA6010A
S11B45B816EA02EA03EA0426036F00395F4B005985F02417A A00290FC5
S11B45D06A008A10480469036902924924F720E96C00CA04564600A7017D
S11B45E807841010B0639074301630263036304FC04261560326116C48
S11B460022460D6C0128098608A7014C006C000704397E44747F42720E
S11B46187F42737F4274CE4267BD45B4CE426CBD45B429E627E4860515
S11B463074426B7426976426A7426B4A26F1744266D7426E74426F19
S11B464B764270F6426B8A1D365B794426A794269794269B84275794204
S11B46607497427379427F704270B6426AB2426F36B64269B2426E36D9
S11B467B642688B24266D2407FB427032322200E7C4275B742683B7423C
S11B469049326B7426A324A426B78403784275794274794273794272A2B
S11B46A826F1B64267B16F8426CC4807F427648784266CE0426CC2B052A24
S11B46C0087E44748B027E44468B02290377E447C0A7E44464534352B4
S11B46D84E00DD00000000000000000000000000000000000000000004B
S9031000EC
```

What is claimed is:

1. Apparatus for determining the nature of an unknown substance comprising, in combination:

means for entering a peak table of the spectrum of an unknown substance into computing apparatus:

means for adjusting said peak table to a first preselected standardized format; said means for adjusting said peak table including means for deleting from the peak table all of the peaks having a transmittance greater than a preselected threshold;

means for comparing the so standardized peak table of the unknown with a first library of chemical structural units contained in memory in said computing apparatus;

means for making a list of the possible chemical structural units most closely corresponding to said unknown substance;

means for readjusting said peak table to a second preselected standardized format; said means for readjusting said peak table including means for deleting from the peak table all peaks having a transmittance greater than a second preselected threshold;

means for forming a file for said unknown substance including data corresponding to said readjusted peak table and to said list of possible chemical structural units;

means for comparing the file of said unknown substance with a second library containing files of known substances contained in memory in said computing apparatus, each known substance having a file containing data corresponding to its respective peak table in said second standardized format and to its respective chemical structural unit; and means for outputting a list of known substances which most closely correspond to said unknown substance.

2. Apparatus for determining the nature of an unknown substance comprising, in combination:

means for entering a peak table of the spectrum of an unknown substance into computing apparatus:

means for adjusting said peak table to a first preselected standardized format; said means for adjusting said peak table including means for correcting said peak table by normalizing to preselected peaks;

means for comparing the so standarized peak table of the unknown with a first library of chemical structural units contained in memory in said computing apparatus;

means for making a list of the possible chemical structural units most closely corresponding to said unknown substance;

means for readjusting said peak table to a second preselected standarized format; said means for readjusting said peak table including means for deleting from the peak table all peaks having a transmittance greater than a second preselected threshold;

means for forming a file for said unknown substance including data corresponding to said readjusted peak table and to said list of possible chemical structural units;

means for comparing the file of said unknown substance with a second library containing files of known substances contained in memory in said computing apparatus, each known substance having a file containing data corresponding to its respective peak table in said second standardized format and to its respective chemical structural unit; and means for outputting a list of known substances which most closely correspond to said unknown substance.

3. Apparatus for determining the nature of an unknown substance comprising, in combination:

means for entering a peak table of the spectrum of an unknown substance into computing apparatus:

means for adjusting said peak table to a first preselected standarized format; said means for adjusting said peak table including means for deleting from the peak table all of the peaks having a transmittance greater than a preselected threshold;

means for comparing the so standarized peak table of the unknown with a first library of chemical structural units contained in memory in said computing apparatus;

means for making a list of the possible chemical structural units most closely corresponding to said unknown substance;

means for readjusting said peak table to a second preselected standarized format; said means for readjusting said peak table including means for restricting the range of wavenumbers in the peak table to a preselected range;

means for forming a file for said unknown substance including data corresponding to said readjusted peak table and to said list of possible chemical structural units;

means for comparing the file of said unknown substance with a second library containing files of known substances contained in memory in said computing apparatus, each known substance having a file containing data corresponding to its respective peak table in said second standardized format and to its respective chemical structural unit; and means for outputting a list of known substances which most closely correspond to said unknown substance.

4. Apparatus for determining the nature of an unknown substance comprising, in combination:

means for entering a peak table of the spectrum of an unknown substance into computing apparatus:

means for adjusting said peak table to a first preselected standarized format; said means for adjusting said peak table including means for correcting said table by normalizing to preselected peaks;

means for comparing the so standarized peak table of the unknown with a first library of chemical structural units contained in memory in said computing apparatus;

means for making a list of the possible chemical structural units most closely corresponding to said unknown substance;

means for readjusting said peak table to a second preselected standarized format; said means for readjusting said peak table including means for restricting the range of wavenumbers in the peak table to a preselected range;

means for forming a file for said unknown substance including data corresponding to said readjusted peak table and to said list of possible chemical structural units;

means for comparing the file of said unknown substance with a second library containing files of known substances contained in memory in said computing apparatus, each known substance having a file containing data corresponding to its respective peak table in said second standardized format and to its respective chemical structural unit; and means for outputting a list of known substances which most closely correspond to said unknown substance.

5. Apparatus for adding data corresponding to a known substance to a library contained in computing apparatus memory comprising in combination:

means for entering a peak table of the spectrum of a known substance into computing apparatus:

means for adjusting said peak table to a first preselect standarized format; said means for adjusting said peak table including means for correcting said peak table by normalizing to preselected peaks;

means for comparing the so standarized peak table of the known substance with a first library of chemical structural units contained in memory in said computing apparatus;

means for making a list of the possible chemical structural units most closely corresponding to said known substance;

means for readjusting said peak table to a second preselected standarized format; said means for readjusting said peak table including means for restricting the range of wavenumbers in the peak table to a preselected range;

means for forming a file for said known substance including data corresponding to said readjusted peak table and to said list of possible chemical structural units, and means for entering said file in storage in the memory of said computing apparatus.

6. Apparatus according to claim 1 or claim 3 wherein said first preselected threshold is of the order of about 95% transmittance.

7. Apparatus according to claim 1 or claim 2 or claim 3 or claim 4 wherein said step of adjusting said peak table to a first preselected standarized format includes means for correcting said peak table for a sloping baseline; means for correcting said peak table using polystyrene or indene calibration data entered by the operator.

8. Apparatus according to claim 1 or claim 2 wherein said second preselected threshold is of the order of about 85% transmittance and said preselected range is from about 1624 to about 600 cm$^{-1}$ wavenumbers.

9. Apparatus according to any one of claims 1, 2, 3 or 4 wherein said means for entering a peak table of the spectrum of an unknown substance includes means for entering said peak table from a spectrophotometer.

10. Apparatus according to any one of claims 1, 2, 3 or 4 wherein said means for entering a peak table of the spectrum of an unknown substance includes means for manually entering said peak table using a keyboard module.

11. Apparatus according to any one of claims 1, 2, 3 or 4 wherein said means for entering a peak table of the spectrum of an unknown substance includes means for entering said peak table using a digitizer module.

12. Apparatus according to any one of claims 1, 2, 3 or 4 wherein said means for entering a peak table of the spectrum of an unknown substance includes means for entering said peak table from a microfloppy disk containing peak tables generated previously.

13. Apparatus according to any one of claims 1, 2, 3 or 4 wherein said means for forming a file for said unknown substance includes means for including data corresponding to the physical state of the unknown and data corresponding to the presence or absence of preselected non-organic elements in said unknown substance, and wherein said files of known substances in said second library contain data corresponding to the physical state of the known substances and data corresponding to the presence or absence of preselected non-organic elements in the known substances, respectively.

14. Apparatus according to claim 13 further comprising means for comparing a file of said unknown substance with the second library containing files of known substances disregarding the possible chemical structural unit data, and means for outputting a second list of known substances which most closely correspond to said unknown substance.

15. Apparatus according to claim 13 further comprising means for comparing the file of said unknown substance with the second library containing files of known substances, and means for outputting a second list of known substances the peaks of which most closely correspond to subsets of peaks of said unknown substance.

16. Appartus according to any one of claims 1, 2, 3 or 4 further comprising means for comparing the file of said unknown substance with the second library containing files of known substances disregarding the possible chemical structural unit data, and means for outputting a second list of known substances which most closely correspond to said unknown substance.

17. Apparatus according to claim 16 further comprising means for comparing the file of said unknown substance with the second library containing files of known substances, and means for outputting a third list of known substances the peaks of which most closely correspond to subsets of peaks of said unknown substance;

said apparatus further comprising means for comparing the file of said unknown substance with the second library containing files of known substances, and means for disregarding the possible chemical structural unit data, and means for outputting a fourth list of known substances the peaks of which most closely correspond to subsets of peaks of said unknown substance.

18. Apparatus according to any one of claims 1, 2, 3 or 4 further comprising means for comparing the file of said unknown substance with the second library containing files of known substances, and means for outputting a second list of known substances the peak of which most closely correspond to subsets of peaks of said unknown substance.

19. Apparatus according to any one of claims 1, 2, 3 or 4 wherein said list of known substances which most closely correspond to said unknown substance includes an indication of the degree of correspondence of said unknown substance to said known substances respectively.

20. Apparatus according to claim 2 or claim 4 wherein said means for adjusting said peak table to a first preselected standardized format includes means for deleting from the peak table all of the peaks having a transmittance greater than a preselected threshold.

21. Apparatus according to claim 3 or claim 4 wherein said means for readjusting said peak table to a second preselected standardized format includes means for deleting from the peak table all of the peaks having a transmittance greater than a second preselected threshold.

22. Apparatus according to claim 21 wherein said means for entering a peak table of the spectrum of an unknown substance includes means for entering said peak table from a spectrophotometer.

23. Apparatus according to claim 21 wherein said means for entering a peak table of the spectrum of an unknown substance includes means for manually entering said peak table using a keyboard module.

24. Apparatus according to claim 21 wherein said means for entering a peak table of a spectrum of an unknown substance includes means for entering said peak table using a digitizer module.

25. Apparatus according to claim 21 wherein said means for entering a peak table of a spectrum of an unknown substance includes means for entering said peak table from a microfloppy disk containing peak tables generated previously.

26. Apparatus according to claim 21 wherein said means for forming a file for said unknown substance includes means for including data corresponding to the physical state of the unknown substance and data corresponding to the presence or absence of preselected non-organic elements in said unknown substance, and wherein said files of known substances in said second library contain data corresponding to the physical state of the known substance and data corresponding to the presence or absence of preselected non-organic elements in the known substances, respectively.

27. Apparatus according to claim 21 further comprising means for comparing the file of said unknown substance with the second library containing files of known substances disregarding the possible chemical structural unit data, and means for outputting a second list of known substances which most closely correspond to said unknown substance.

28. Apparatus according to claim 21 further comprising means for comparing the file of said unknown substance with the second library containing files of known substances, and means for outputting a second list of known substances, the peaks of which most closely correspond to subsets of peaks of said unknown substance.

29. Apparatus for adding data corresponding to a known substance to a library contained in computing apparatus memory comprising in combination:
    means for entering a peak table of the spectrum of a known substance into computing apparatus:
    means for adjusting said peak table to a first preselect standardized format; said means for adjusting said peak table including means for deleting from the peak table all of the peaks having a transmittance greater than a preselected threshold;
    means for comparing the so standardized peak table of the known substance with a first library of chemical structural units contained in memory in said computing apparatus;
    means for making a list of the possible chemical structural units most closely corresponding to said known substance;
    means for readjusting said peak table to a second preselected standardized format; said means for readjusting said peak table including means for deleting from the peak table all peaks having a transmittance greater than a second preselected threshold;
    means for forming a file for said known substance including data corresponding to said readjusted peak table and to said list of possible chemical structural units, and
    means for entering said file in storage in the memory of said computing apparatus.

30. A method for determining the nature of an unknown substance comprising, in combination, the steps of:
    entering a peak table of the spectrum of an unknown substance into computing apparatus:
    adjusting said peak table to a first preselected standardized format; said step of adjusting said peak table including a step of deleting from the peak table all of the peaks having a transmittance greater than a preselected threshold;
    comparing the so standardized peak table of the unknown with a first library of chemical structural units contained in memory in said computing apparatus;
    making a list of the possible chemical structural units most closely corresponding to said unknown substance:
    readjusting said peak table to a second preselected standardized format; said step of readjusting said peak table including a step of deleting from the peak table all peaks having a transmittance greater than a second preselected threshold;
    forming a file for said unknown substance including data corresponding to said readjusted peak table and to said list of possible chemical structural units;
    comparing the file of said unknown substance with a second library containing files of known substances contained in memory in said computing apparatus, each known substance having a file containing data corresponding to its respective peak table in said second standardized format and to its respective chemical structural unit; and
    outputting a list of known substances which most closely correspond to said unknown substance.

31. A method for determining the nature of an unknown substance according to claim 30 wherein said step of adjusting said peak table further includes the step of correcting said peak table by normalizing to preselected peaks; and said step of readjusting said peak table further includes the steps of restricting the range of wavenumbers in the peak table to a preselected range.

* * * * *